(12) United States Patent
Murata

(10) Patent No.: US 6,756,525 B1
(45) Date of Patent: *Jun. 29, 2004

(54) METHOD FOR PRODUCING TEMPERATURE-TOLERANT PLANTS

(75) Inventor: Norio Murata, Aichi-ken (JP)

(73) Assignee: Suntory Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/091,885

(22) PCT Filed: Dec. 27, 1996

(86) PCT No.: PCT/JP96/03873

§ 371 (c)(1),
(2), (4) Date: Jun. 26, 1998

(87) PCT Pub. No.: WO97/24026

PCT Pub. Date: Jul. 10, 1997

(30) Foreign Application Priority Data

Dec. 28, 1995 (JP) .............................. 7-343354
Mar. 27, 1996 (JP) .............................. 8-97534

(51) Int. Cl.⁷ ........................ C12N 15/82; C12N 15/90; C12N 5/04; A01H 5/00; A01H 1/00
(52) U.S. Cl. ...................... 800/289; 435/419; 435/468; 800/298; 800/306; 800/320
(58) Field of Search ............................... 800/289, 278, 800/298, 306, 320; 435/172.1, 172.3, 410, 419, 468

(56) References Cited

U.S. PATENT DOCUMENTS 6,281,412 B1 * 8/2001 Murata ....................... 800/288

FOREIGN PATENT DOCUMENTS

| EP | 818138 A1 | 1/1998 |
| WO | WO 9414970 | 7/1994 |
| WO | WO 9826081 | 6/1998 |

OTHER PUBLICATIONS

M. D. Mamedov et al., *FEBS Lett.*, vol. 294, No. 3, pp. 271–274 (1991).
N. Murata et al., *FEBS Lett.*, vol. 296, No. 2, pp. 187–189 (1992).
B. Rathinasabapathi et al., *Planata*, 193:155–162 (1994).
K. Holmström et al., *The Plant Journal*, 6(5), pp. 749–758 (1994).
Patchcharaporn, et al., Chemical Abstracts, vol. 126, Jun. 2, 1997, XP002087537.
Murata N. et al., Phys. Stresses Plants: Genes Their Prod. Tolerance, pp. 55–63, Sep. 1995, XP002062848.
Mamedov M. et al., Database Biosis Biosciences Information Service, (abstract), 1993, XP002087538.
Deshnium et al., Embl Accession, Feb. 27, 1995, XP002087232.
Holmstroem et al., The Plant Journal, vol. 6, 1994, XP002034433 pp 749–758.
Kishitani et al., Database Biosis Biosciences Information Service, 1994, XP002087539.
Rathinasabapathi et al., Planta, vol. 193, 1994, XP002034434 pp 155–162.
Palva et al., Sep. 24–27, 1995 pp. 187–198, XP002044597.
Paleg et al., Biological Abstracts, vol. BA72, (Abstract) 1981, XP002087536.
Zhao et al., Database Biosis Biosciences Info. Service, (Abstract), 1992, XP002087540.
Ko et al., Database Biosis Biosciences Info. Service, (Abstract), 1994, XP002087541.
Rhodes et al., Annu. Rev. Plant Physiol. Plant Mol. Biol., 1993 vol. 44, pp. 357–384, XP002087532.
Kodama et al., Plant Physiology, vol. 105, pp. 601–605, Jan. 1, 1994, XP002001002.
Lee et al., Plant Journal, vol. 8, pp. 603–612, Oct. 1, 1995, XP002003021.
Derwent Publications Ltd., Database WP1, Oct. 15, 1996, XP002062849.
Wada et al., Nature, vol. 347, Sep. 13, 1990, pp. 200–203, XP002087535.
Patcharaporn Deshnium et al., *Plant Molecular Biology*, vol. 29, pp 897–907, 1995.
Mika Nomura et al., *Plant Physiol*, vol. 107, pp. 703–708, 1995.
Kevin L. Rozwadowski et al., *Journal of Bacteriology*, vol. 173, No. 2, pp. 472–478, 1991.
Bartels et al. Plant, Cell and Environment, vol. 17, pp. 659–667, 1994.*
Deshnium et al. Plant Molecular Biology, vol. 29, pp. 897–907, 1995.*
Holmstrom et al. The Plant Journal, vol. 6, pp. 749–758, 1994.*
Rozwadowski et al. Journal of Bacteriology, vol. 173, pp. 472–478, 1991.*
Rozwadowski et al., Journal of Bacteriology, vol. 173, pp. 472–478, 1991.
Kishitani et al. Plant Cell and Environment, vol. 17, pp. 89–95, 1994.*
Ko et al. Journal of Bacteriology, vol. 2, pp. 426–431, 1994.*
Zhao. et al. Journal of Plant Physiology, vol. 140, pp. 541–543, 1992.*

* cited by examiner

Primary Examiner—Ashwin Mehta
(74) Attorney, Agent, or Firm—Birch, Stewart, Kolasch & Birch, LLP

(57) ABSTRACT

A method for producing temperature-tolerant plants, which comprises transforming a plant with a recombinant vector carrying a gene encoding choline oxidase, as well as temperature-tolerant plants produced by said method or progenies thereof having the same properties.

9 Claims, 20 Drawing Sheets

METHOD FOR PRODUCING TEMPERATURE-TOLERANT PLANTS

This application is the national phase under 35 U.S.C. §371 of prior PCT International Application No., PCT/JP96/03873, which has an International filing date of Dec. 27, 1996, which designated the United States of America, the entire contents of which are hereby incorporated by reference.

FIELD OF THE INVENTION

The present invention relates to a method for producing plants with novel properties, more specifically, a method for producing temperature-tolerant plants which are highly resistant to environmental stress.

PRIOR ART

Many organisms adapt themselves to severe environmental stress by synthesizing and accumulating a specific compound called "compatible solute" in their cytoplasm to protect themselves against such stress. Environmental stress to which organisms have been shown to adapt themselves by such a mechanism include salts (Imhoff et al., FEMS Microbiol. Rev. 39:57–66, 1986; Mackay et al., J. Gen. Microbiol. 130:2177–2191, 1984; Rhodes and Hanson, Annu. Rev. Plant Physiol. Plant Mol. Biol. 44:357–384, 1993), dehydration (Yancy et al., Science 217:1214–1222, 1982) and low temperatures (Ko et al., J. Bacteriol. 176:426–431, 1994).

Among those compatible solutes, glycine betaine (hereinafter referred to as betaine) is widely distributed in higher plants (Robinson and Jones, Aust. J. Plant Physiol. 13:659–668, 1986), bacteria (Csonka, Microbiol. Rev. 53:121–147, 1989) and animals (Garcia-Perez and Burg, Physiol. Rev. 71:1081–1115, 1991; Lever et al., Biochim. Biophys. Acta. 1200:259–264, 1994). As shown in FIG. 1, betaine is a bipolar compound having a positive charge and a negative charge in its molecules (Rhodes and Hanson, Annu. Rev. Plant Physiol. Plant Mol. Biol. 44:357–384, 1993). A long discussion regarding the physiological functions of betaine has suggested that betaine may protect cells by maintaining an osmotic balance with the environment (Robinson and Jones, Aust. J. Plant Physiol. 13:659–668, 1986) and that betaine may stabilize higher-order structures of proteins (Bernard et al., Acad. Sci. 111, 307:99–104, 1988; Papageorgiou and Murata, Phtosynth. Res. 44:243–252, 1995). However, betaine is not exclusively synthesized in cells under salt stress or dehydration stress. Thus, it could not be concluded that betaine has a direct effect on the protection of cells against such stress.

In *Escherichia coli* and spinach (*Spinacia oleracea*), betaine is biosynthesized from choline via two steps of oxidation as shown in FIG. 1. On the other hand, choline oxidase obtained from the gram-positive soil bacterium *Arthrobacter globiformis* can oxidize choline to betaine in one-step oxidation reaction (Ikuta, S. et al., J. Biochem. 82:1741–1749, 1977).

In an attempt to study a direct effect of betaine, we isolated the coda gene encoding a novel choline oxidase which catalyzes oxidation from choline to betaine (Japanese Society of Plant Physiologist, Annual meeting of 1994, the 34th Symposium held Mar. 28–30, 1994) and integrated it into cells of the cyanobacterium strain Synechococcus PCC7942 and brassicaceous plants, thus succeeded in obtaining salt-tolerant and/or osmotolerant plants (Japanese Patent Application No. 106819/95). This confirmed that betaine functions to protect organisms against salt stress.

However, no report has shown that betaine confers temperature tolerance on plants or bacteria.

It is an object of the present invention to produce plants that are tolerant to environmental changes such as high temperatures or low temperatures by gene recombination techniques.

DISCLOSURE OF THE INVENTION

As a result of careful study to solve the above problems, we succeeded in obtaining temperature-tolerant plants by integrating and expressing a gene encoding choline oxidase in cyanobacteria, brassicaceous plants and gramineous plants.

Accordingly, the present invention provides a method for producing temperature-tolerant plants, which comprises transforming a plant with a recombinant vector carrying a gene encoding choline oxidase.

The present invention also provides temperature-tolerant plants produced by said method or progenies thereof having the same properties.

THE BEST EMBODIMENTS OF THE INVENTION

Figure 1:
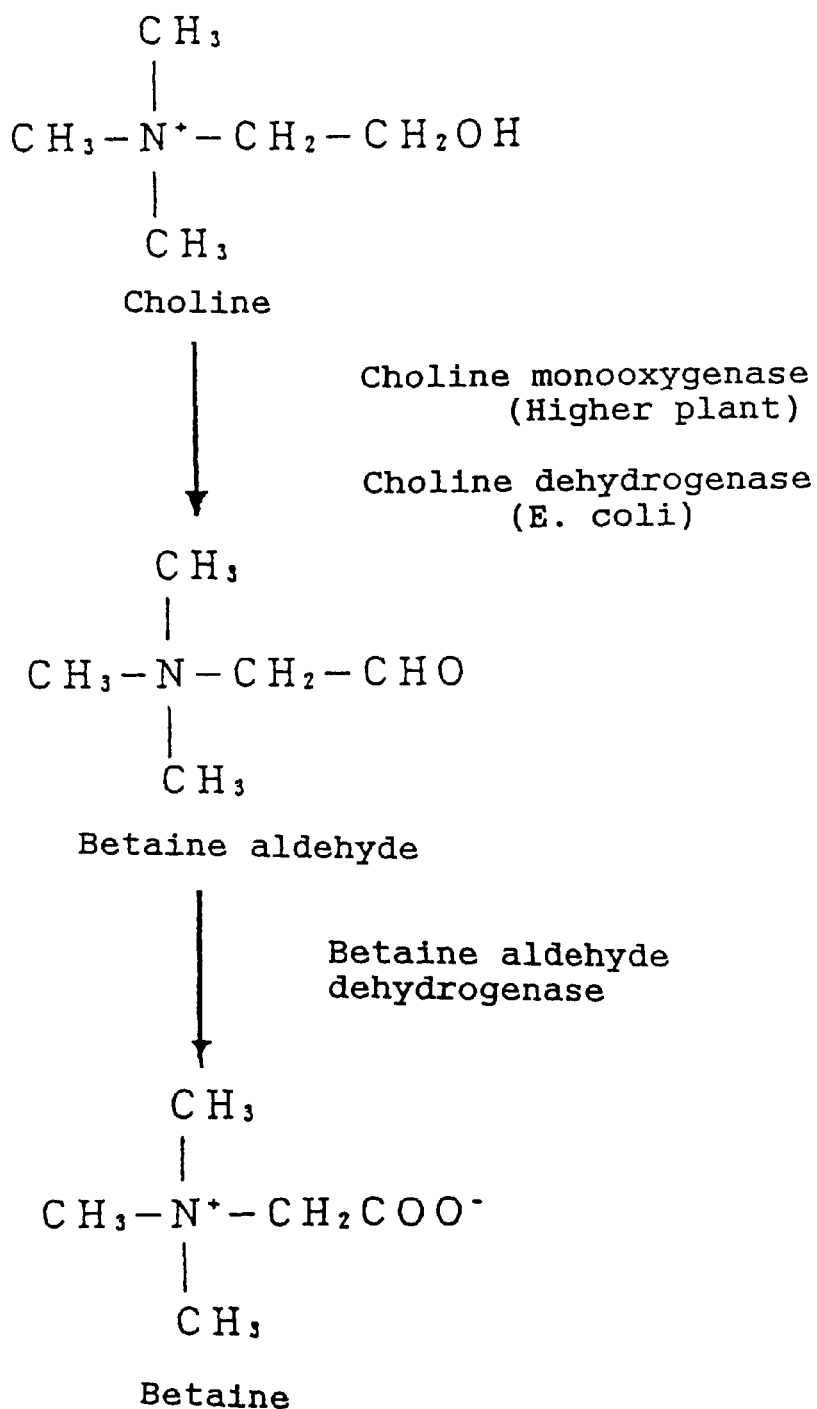
FIG. 1: Schematic representation showing the oxidation process from choline to betaine.

As used herein, temperature tolerance means an ability of a transformed plant to grow at higher or lower temperatures than the temperatures which normally allow non-transformed plants to grow.

The gene encoding choline oxidase used in the present invention is a gene which encodes a protein capable of converting choline into betaine in a one-step reaction and which may be derived from gram-positive soil bacteria of the genus Arthrobacter. For example, it may be preferably derived from Arthrobacter globiformis and Arthrobacter pascens, especially Arthrobacter globiformis.

We cloned the codA gene encoding choline oxidase from Arthrobacter globiformis and determined its nucleotide sequence. The codA gene contains an open reading frame of 1641 bp, which encodes 547 amino acids. The nucleotide sequence and amino acid sequence of the codA gene are shown as SEQ ID NO: 1 in Sequence Listing.

Such a gene encoding choline oxidase can be integrated into appropriate vectors to transform a plant. Then, an appropriate promoter or a sequence involved in the expression of a character can be introduced into these vectors to express the gene in the plant.

The gene encoding choline oxidase may include not only the nucleotide sequence encoding the amino acid sequence of SEQ ID NO: 1 in Sequence Listing but also nucleotide sequences in which one or more amino acids are added to, deleted from or substituted for said amino acid sequence provided that they encode a protein having choline oxidase activity.

The method of the present invention can confer temperature tolerance on a wide variety of plants ranging from cyanobacteria to higher plants. Cyanobacteria are widely used as model organisms of higher plants because they have basically the same photosynthetic mechanism as that of higher plants and they can be readily transformed to give results in a short time. Some easy-to-transform cyanobacteria readily take up extracellular DNA into their cells to cause efficient recombination. Such cyanobacteria include Synechococcus PCC7942, Synechococcus PCC6301 (ATCC 27144) and Synechocystis PCC6803 (ATCC 27184) (Protein, Nucleic Acid, Enzyme, Vol. 35, No. 14, pp. 2542–2551, 1991; Crit. Rev. Microbiol. Vol. 13, No. 1, pp. 111–132, 1985).

Higher plants include dicotyledons and monocotyledons. In the examples described below, highly temperature-tolerant plants could be obtained from a brassicaceous plant as a dicotyledon, but it is not limitative and other families and genera of dicotyledons may be used. The method of the present invention may also be applicable to monocotyledons. It was found that a monocotyledonous plant rice, which originally lacks betaine-synthesizing ability, gained this ability after transformation by the method of the present invention.

The vector into which the choline oxidase-coding gene can be integrated and the method for transformation and selection of transformed plants can be appropriately chosen dependent on the nature of the plant to be transformed, including plant cells.

For example, a plasmid such as pUC303 can be used for cyanobacteria. Then, transformants having desired properties can be selected by an antibiotic-resistant gene inserted into the plasmid. According to the present invention, plants showing tolerance to both of high and low temperatures were successfully obtained by transforming the cyanobacterium Synechococcus PCC7942 with the codA gene encoding choline oxidase derived from Arthrobacter globiformis.

When the Synechococcus PCC7942 transformed with the codA gene was cultivated in BG11 medium supplemented with choline chloride, the transformed Synechococcus was found to take up exogenously supplied choline to convert it into betaine and accumulate betaine up to a level of about 80 mM. However, such accumulation was not observed with a control group of Synechococcus strain lacking the codA gene.

When the Synechococcus strain transformed with the codA gene and a control group of non-transformed strain were cultivated in BG11 medium supplemented with choline chloride at 42° C. to examine their reaction to high temperatures, the transformed Synechococcus stopped growing for a day and then began to grow again. The non-transformed control group did not grow at all at 42° C. When they were cultivated at 20° C. to examine their reaction to low temperatures, the transformed strain grew slowly for 4 days but then began to grow rapidly. However, the non-transformed control group still grew very slowly even after 4 days. A growth test using a solid medium also showed that the transformed strain grew well at both high and low temperatures as compared with the non-transformed strain. These results revealed that the Synechococcus strain transformed with the codA gene grows significantly better than the non-transformed strain both at high and low temperatures.

It has been pointed out that betaine not only acts as an osmoprotectant but also plays an essential role in the protection of a photosynthetic mechanism in photoautotrophic organisms (Murata et al., FEBS Lett. 296:187–189, 1992). Thus, the Synechococcus strain transformed according to the present invention and the non-transformed strain were cultivated in the dark at various low temperatures to examine temperature tolerance of photosynthesis. As a result, a great difference was observed between the transformed strain and non-transformed strain in photosynthetic oxygen release level and inactivation of electron transport mediated by photochemical system II in cells at low temperatures. Namely, photosynthetic oxygen release level of the transformed strain was more tolerant to low temperatures than that of the non-transformed strain. Electron transport activity mediated by photochemical system II in cells of the transformed strain was also more tolerant to low temperatures than that of the non-transformed strain, i.e. the activity of the non-transformed strain was lowered to 50% of the original level at 5° C. while the activity of the transformed strain remained at almost the original level at 5° C. and began to decrease below 5° C.

It has previously been known that the optimal temperature for growth of Synechococcus PCC7942 ranges from 30 to 38° C. Thus, it is deduced that the non-transformed strain was inhibited from cell growth by denaturation of the structures of some proteins at such a high temperature as 42° C. However, the transformed strain carrying the codA gene could grow probably because about 80 mM betaine accumulated in cells prevented denaturation of proteins. At 20° C., the non-transformed strain could not grow, but the transformed strain in which the codA gene had been integrated could grow. This may also result from accumulation of betaine. Further, betaine accumulation in cytoplasm is thought to enhance the tolerance of cyanobacterial cells to low temperatures in the dark. However, the present invention is not restricted to such an action mechanism.

These results mean that excellent tolerance to both high and low temperatures has been conferred on the Synechococcus transformed with the gene encoding choline oxidase according to the method of the present invention.

Dicotyledons may be transformed by gene transfer techniques using protoplasts or a part of tissue. In case of the gene transfer using tissue fragments, the Ti plasmid from Agrobacterium may be used. Tissue fragments of a callused plant may be infected with Agrobacterium into which the choline oxidase-coding gene has been integrated, selected by resistance to an antibiotic such as kanamycin, and then differentiated in shoots to give a transformed plant.

In the present invention, a highly temperature-tolerant plant could be obtained by transforming the brassicaceous plant Arabidopsis thaliana with the choline oxidase-coding gene as follows.

A binary vector plasmid pGAH-codA carrying the codA gene was prepared and integrated into Agrobacterium tumefaciens EHA101 bearing the Ti plasmid. Hypocotyl calli of Arabidopsis were infected with the resultant Agrobacterium EHA101 (pGAH/codA) incorporating the codA gene, then shoots were formed and selected by kanamycin and hygromycin resistance to induce roots and to form seeds. The plants obtained from the resultant heterozygous T2 seeds were self-fertilized to give homozygous T3 individuals, which were sown to form a transformed plant.

Thus obtained transformed plant showed that choline oxidase had been transported to chloroplasts. When choline and betaine levels in leaf were measured, only choline was observed in the wild-type plant while both of choline and betaine were observed in the transformed plant, suggesting that betaine is accumulated in plants by transfer of the codA gene. The transformed plant showed a remarkable temperature tolerance as compared with the wild type.

The monocotyledonous plant rice (Oryza sativa L. cv. Nippon bare) can be transformed with, for example, two chimeric codA genes prepared on the plasmid pUC119, which are localized in cytosol or plastid after translation under transcriptional control of the cauliflower mosaic under transcriptional control of the cauliflower mosaic virus 35S promoter. Both of the chimeric genes include a rice-derived intron in the 5' non-translated sequence to enhance expression level.

A transformed rice can be produced by the following procedure. Namely, a transformed plant can be obtained by introducing said chimeric codA genes into suspension culture cells from scutellum calli of rice seeds together with a selection marker hygromycin-resistant gene by a particle gun device, then selecting the transformed calli based on antibiotic resistance, and redifferentiating them into a plant.

Although the wild-type rice lacks betaine-synthesizing ability, the rice transformed by the method of the present invention gained betaine-synthesizing ability. The transformed rice expressing the codA gene grew equally to the non-transformed plant without showing any apparent abnormality under both of geoponic and hydroponic conditions. This may conclude that hydrogen peroxide formed as a by-product of betaine synthesis was efficiently detoxified in cells. In view of the relation between acquisition of betaine-synthesizing ability and temperature tolerance in cyanobacteria and dicotyledons, the transformed rice obtained by the method of the present invention can be expected to also have gained temperature tolerance. This is the first case in which rice has gained betaine-synthesizing ability through genetic engineering techniques.

When recovery of photochemical system II of transformed and non-transformed plants after placed in dark conditions was compared in experiments using Synechococcus, the transformed plant recovered more rapidly, indicating that the presence of betaine accelerated recovery of photochemical system II. It was also shown that photosynthesis of the transformed plant is more tolerant to low temperatures than that of the non-transformed plant. In view that any great difference was not found in membrane lipid and protein between the transformed plant and non-transformed plant, the protection of photochemical system II observed in the transformed plant at low temperatures seemed to be an effect of betaine.

The scope of the present invention covers not only temperature-tolerant plants produced as described above or progenies thereof having the same properties, but also plant cells (for example, callus cultured cells) and plant portions (for example, flowers, seeds, fruits, tubers, etc.) obtained therefrom as well as progenies thereof.

According to the present invention, temperature-tolerant transformed plants that are highly resistant to environmental stresses can be obtained. The method of the present invention can be used to produce plants that can grow under high-temperature or low-temperature conditions under which plants normally can not grow. The range of plants on which can be conferred temperature tolerance by the method of the present invention is very wide, from photosynthetic bacteria to higher plants. Especially, the present invention is industrially very useful, because it is the first case in which stable transformed plants were obtained from monocotyledons including most main crops and confirmed for their betaine synthesis.

The method for producing temperature-tolerant plants according to the present invention is very useful, because it can be used to produce plants that can tolerate both high and low temperatures. The following examples illustrate the present invention more in detail, but are not construed as limiting the scope thereof.

EXAMPLES

Example 1

Transformation of the Cyanobacterium Synechococcus PCC7942 With the CodA Gene (1) Cloning of the CodA Gene The choline oxidase gene was isolated from Arthrobacter globiformis by the method described in the Abstracts of Oral Reports published in the 34th symposium of the annual meeting of the Japanese Society of Plant Physiologists, 1994. In brief, 1) choline oxidase is fragmented with cyanogen bromide, 2) the N-terminal amino acid sequence of an appropriate fragment is determined, 3) appropriate portions are selected from said amino acid partial sequence to synthesize oligonucleotides corresponding thereto, 4) a partial sequence of the choline oxidase gene is amplified by PCR (Polymerase Chain Reaction) using these oligonucleotides as primers, 5) the amplified partial sequence of the choline oxidase gene is used as a probe to screen the genomic DNA library of Arthrobacter globiformis.

Thus obtained positive clones were subcloned into the plasmid pBluescript (SK+) (Stratagene) to isolate positive clones, which were subjected to Southern blot analysis. A 3.6 kbp XbaI-XhoI fragment which hybridized to said probe was subcloned into pBluescript and mapped with restriction enzymes. The nucleotide sequence of the region spanning from the first SalI-site to XhoI-site (about 2.5 kbp) was determined.

The results showed that the choline oxidase gene contains an open reading frame of 1641 bp which encodes a polypeptide of 547 amino acid residues. The amino acid sequence and the nucleotide sequence of the choline oxidase-coding gene are shown as SEQ ID NO: 1 in Sequence Listing.

(2) Transformation of Synechococcus PCC7942 with the CodA Gene

The plasmid pBluescript carrying the codA gene was digested with the restriction enzymes BstEII (at position −40 from the translation origin) and SmaI (downstream of the stop codon). The BstE II-cohesive end was filled with a Klenow fragment (Takara, Tokyo, Japan). The blunt-ended fragment containing the coding region of the codA gene and a putative ribosome binding site was inserted into the SmaI site of the plasmid pAM1044. The correct orientation of the gene, which seems to be expressed under control of the conII promoter of pAM1044, was confirmed by restriction enzyme analysis. The conII promoter is a consensus sequence of E. coli promoters, containing the nucleotide sequences TTGGACA (−35) and TATAAT (−10).

The plasmid pAM1044 and the plasmid containing the codA gene were used to transform Synechococcus PCC7942 by the method of Elhai et al. The resultant transformant was designated as the strain PAMCOD. As a control, Synechococcus PCC7942 was transformed with pAM1044 alone and designated as the strain PAM.

Figure 2A:
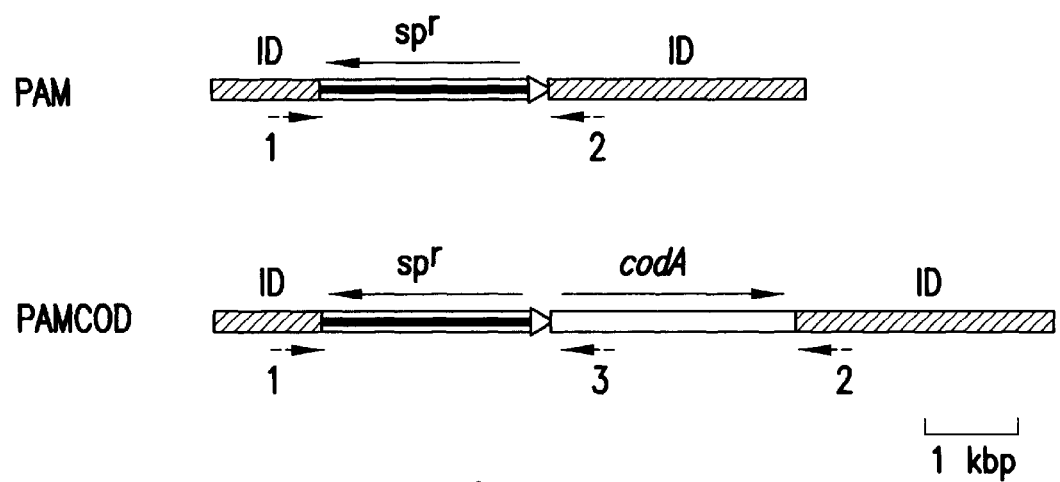
FIG. 2A: Schematic representation showing constructs used for transformation of Synechococcus PCC7942. PAM refers to Synechococcus PCC7942 transformed with pAM1044, and PAMCOD refers to Synechococcus PCC7942 transformed with pAM1044 carrying the codA gene. Dashed arrows indicate primers used for PCR. Triangles represent the conII promoter. Arrows indicate the orientation of genes.

Selection of transformants was performed on BG11 agar plates containing 30 µg/ml of spectinomycin. After several passages of a single colony to fresh BG11 plates containing spectinomycin, the complete insertion of the spectinomycin-resistant gene and the codA gene into all the copies of chromosomes was confirmed by PCR (Polymerase Chain Reaction) using the primers shown in FIG. 2A. The complete insertion of the spectinomycin-resistant gene and the codA gene into Synechococcus chromosomes was confirmed by PCR using a combination of primers 1 and 2.

Cultivation of the strains PAMCOD and PAM was performed in BG 11 medium (Stanier et al., Bacteriol. Rev. 35:171–205, 1971) supplemented with 1 mM choline chloride (Kitayama Chemical) with aeration at 1% $CO_2$ at 30° C. under illumination with an incandescent lamp of 70 µE $m^{-2}s^{-1}$. Logarithically growing cells were used in all the experiments described below. Photosynthetic activity was measured at a cell density adjusted to a chlorophyll concentration of 5–10 µg/ml.

Example 2

Confirmation of the gene Inserted Into Transformants

DNAs from the strains of wild-type, PAM and PAMCOD of Synechococcus PCC7942 were used as templates for PCR, and the amplified products were analyzed by SDS-PAGE. The results are shown in FIG. 2B.

Figure 2B:
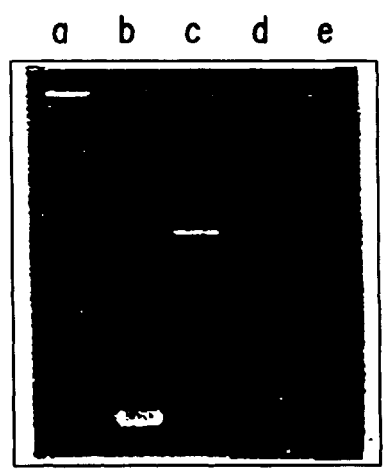
FIG. 2B: SDS-PAGE (photograph of electrophoresis) showing the complete replacement of chromosomes by the spectinomycin-resistant gene and coda gene in DNA of Synechococcus PCC7942. Lane a: λ-HindIII/φx174-HaeIII fragment; Lane b: the wild-type strain of Synechococcus PCC7942; Lane c: the strain PAM; Lanes d and e: the strain PAMCOD (Lanes b, c and d show the results of PCR with primers 1 and 2, and lane e shows the results of PCR with primers 1 and 3).

PCR of DNA from the wild-type strain produced an amplified product of about 400 bp (FIG. 2B, lane b). PCR using DNA from the strain PAM as a template produced a band of about 2.4 kb, indicating that pAM1044 had been inserted into chromosomes. The band of about 400 bp as observed in the wild-type strain does not exist, indicating that native chromosomes had been completely replaced by mutant chromosomes in the strain PAM.

When DNA from PAMCOD was used as a template, the band corresponding to wild-type chromosomes was not observed (FIG. 2B, lane c). However, the predicted band of about 4.1 kb was not amplified, either, probably due to the large size of the insert and the high GC content in the codA sequence. Therefore, primer 3 corresponding to the coding region of the codA gene (FIG. 2A) was used in combination with primer 1. The predicted band of about 2.6 kb was amplified (FIG. 2B, lane d), indicating that the codA gene exists in chromosomes of the strain PAMCOD.

Example 3

Expression of the CodA Gene in the Synechococcus Strain PAMCOD

Figure 3:
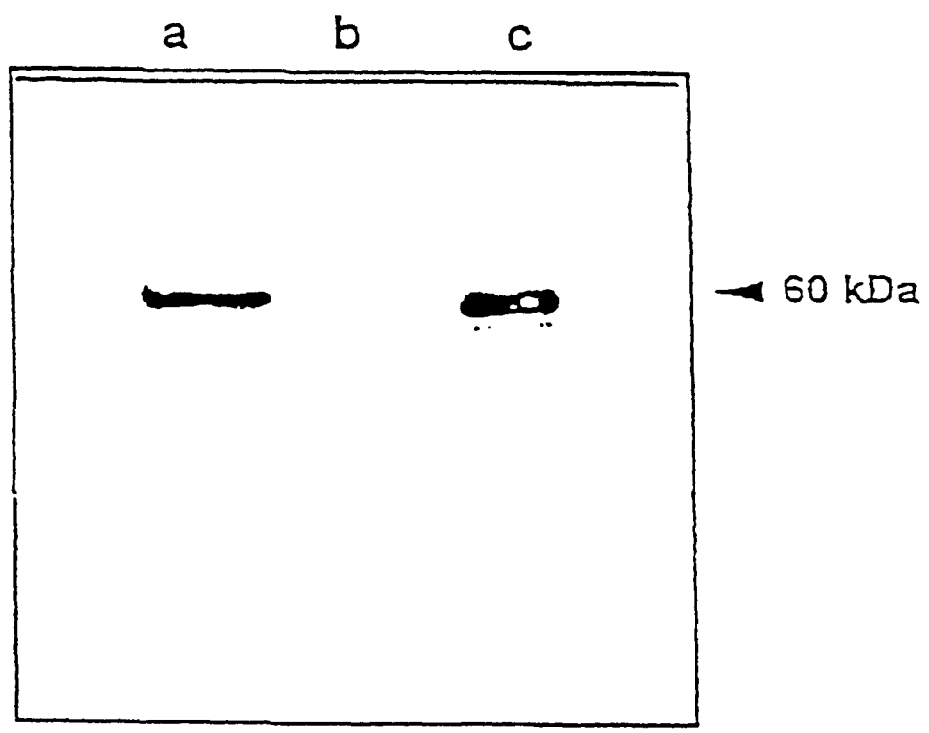
FIG. 3: Western blot analysis (photograph of electrophoresis) showing the expression of choline oxidase in the Synechococcus PCC7942 strains PAM and PAMCOD. Lane a: protein extracts from the strain PAMCOD; Lane b: protein extracts from the strain PAM; Lane c: purified choline oxidase.

The expression of the codA gene in the strain PAMCOD obtained in Example 1 was examined by Western blot analysis using a polyclonal antiserum to purified choline oxidase. The results are shown in FIG. 3. Signals were detected at 60 kDa in protein extracts from the strain PAMCOD (lane a) and purified choline oxidase (lane c). This signal was not detected in protein extracts from the strain PAM (lane b). This result confirmed that the codA gene had been expressed in Synechococcus PCC7942 under control of the conII promoter.

Example 4

Analysis of Betaine Concentration in Cells

Transformed cells were grown in one liter of BG11 medium supplemented with 5 mM choline chloride. Salt stress was given by adding NaCl at various concentrations. The harvested cells were treated with 1M $H_2SO_4$ at 25° C. for 20 hours and betaine was recovered from the mixture by the periodate precipitation technique (Wall, J. S. et al., Analyt. Chem. 32:870–874, 1960). Betaine periodate was dissolved in 1 ml of methanol-$d_4$ (Wako) containing 2 mM 2-methyl-2-propanol (Wako) as an internal standard. This solution was measured for $^1H$ NMR spectra in an NMR tube using a Bruker AMX 360 Wb. Betaine was quantified by comparing the integrated peaks with a standard curve.

Betaine concentration in cells of the strain PAMCOD was determined on the basis of cell volumes estimated from the electron micrograph of negatively stained cells. The cytoplasm of a single cell had a cylindrical shape of 2.14 $\mu m$ in length and 0.82 $\mu m$ in diameter and the cell volume was estimated to be approximately 1.13 $\mu m^3$.

As a result, betaine concentration in cells of the strain PAMCOD was calculated at about 80 mM. However, no trace of betaine could be detected in the strain PAM lacking the codA gene.

Example 5

Growth Under High- and Low-temperatures Stresses (1) Growth Tests in a Solid Medium

Growth at High Temperatures

Figure 4A:
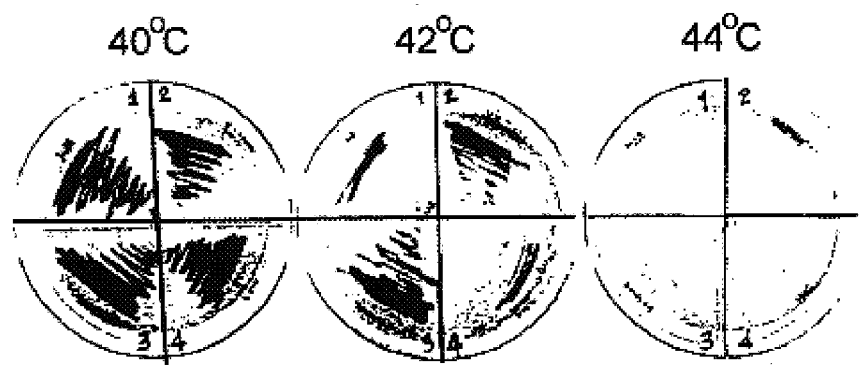
FIG. 4(A–B): Results of growth of Synechococcus PCC7942 strains grown at various temperatures for 10 days on an agar plate in BG 11 medium supplemented with 1 mM choline chloride (photographs showing morphology of organisms). 1 and 4: PAM strain; 2 and 3: PAMCOD strain.

The Synechococcus strains PAM and PAMCOD were transferred to an agar plate in BG11 medium supplemented with 1 mM choline chloride and observed for growth at 40° C., 42° C. and 44° C. The results are shown in FIG. 4A. Both strains almost equally grew at 40° C. Neither strain grew at 44° C. At 42° C., the strain PAM grew very slowly while the strain PAMCOD grew very well.

Growth at Low Temperatures

Figure 4B:
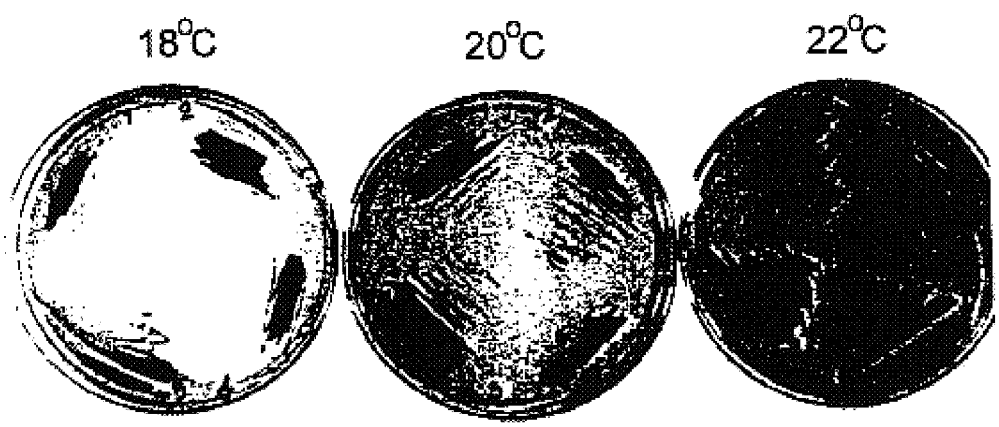

The Synechococcus strains PAM and PAMCOD were transferred to an agar plate in BG11 medium supplemented with 1 mM choline chloride and observed for growth at 22° C., 20° C. and 18° C. The results are shown in FIG. 4B. Both strains almost equally grew at 22° C. At 20° C., the strain PAMCOD grew more rapidly than the strain. Neither strain grew well at 18° C.

(2) Growth Tests in a Liquid Medium

Growth at High Temperatures

Figure 5B:
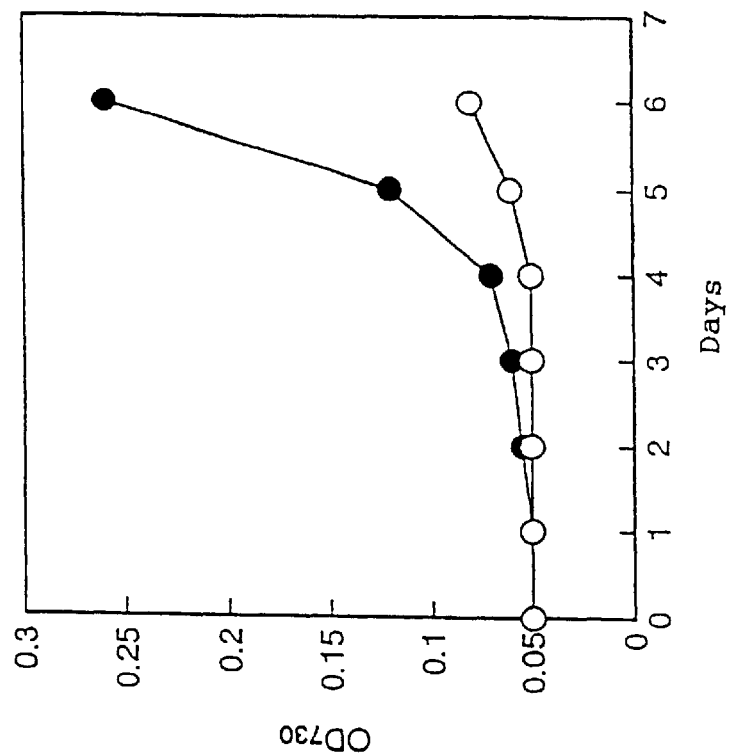
FIG. 5: Growth of the Synechococcus strains PCC7942 PAM (○) and PAMCOD (●) in BG11 medium supplemented with 1 mM choline chloride under illumination. A: Growth at 42° C.; B: Growth at 20° C.
Figure 5A:
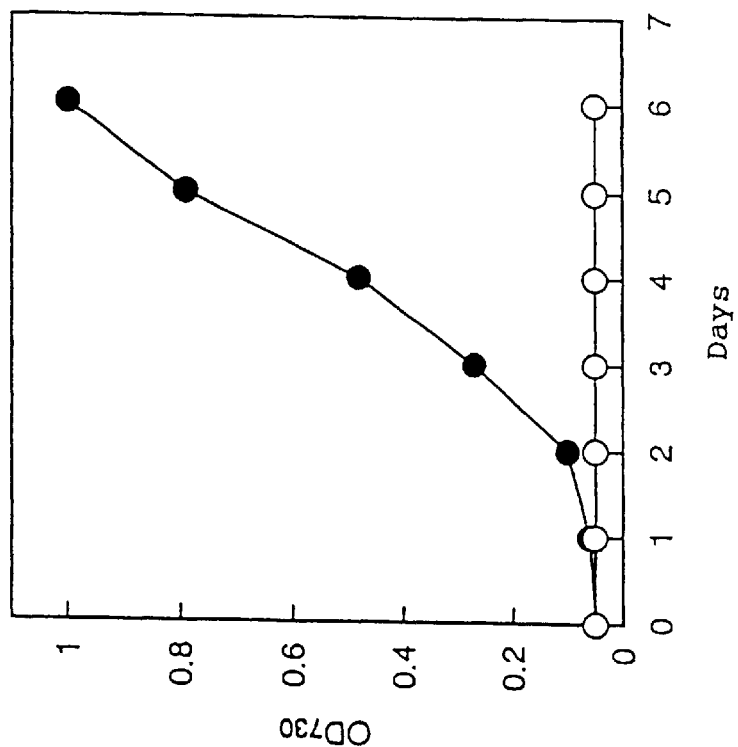

Cells of the Synechococcus strains PAM and PAMCOD preliminarily grown in BG11 medium supplemented with 1 mM choline chloride at 30° C. were transferred to 42° C. and assessed for growth by monitoring the turbidity at a wavelength of 730 nm. The results are shown in FIG. 5A. Cells of the strain PAMCOD stopped growing on the first day, but then resumed to grow. However, cells of the strain PAM did not grow at all.

Growth at Low Temperatures

Cells of the Synechococcus strains PAM and PAMCOD preliminarily grown in BG11 medium supplemented with 1 mM choline chloride at 30° C. were transferred to 20° C. and assessed for growth by monitoring the turbidity at a wavelength of 730 nm. The results are shown in FIG. 5B. Cells of the strain PAMCOD grew slowly for 4 days, but then began to rapidly grow. However, cells of the strain PAM still grew slowly after 4 days.

Example 6

Photosynthetic Activity Under Low-temperature Stress

Inactivation of photosynthetic oxygen release induced by low-temperature stress was examined. Cells of the strains PAM and PAMCOD preliminarily grown at 30° C. were grown in the dark at various temperatures. After then, photosynthetic oxygen release activity was measured at 30° C. in the presence of 1 mM $NaHCO_3$ or in the presence of 1,4-benzoquinone and 1 mM $K_3Fe(CN)_6$ using a Clark-type oxygen electrode.

Photosynthetic Activity at Low Temperatures

Cells were grown in the dark at various temperatures from 0 to 20° C. for 1 hour, then at 30° C. for 5 minutes. After growth, photosynthetic oxygen release activity was measured in the manner described above. Cells of the strains PAM and PAMCOD showed absolute activities of photosynthetic oxygen release of 387±23 and 379±19 $\mu mole$ $O_2$/mg chlorophyll/hour, respectively, in the presence of $CO_2$, and the absolute activities of photosynthetic oxygen release of 802±36 and 740±82 $\mu mole$ $O_2$/mg chlorophyll/hour, respectively, in the presence of 1,4-benzoquinone and $K_3Fe(CN)_6$.

Figure 6A:
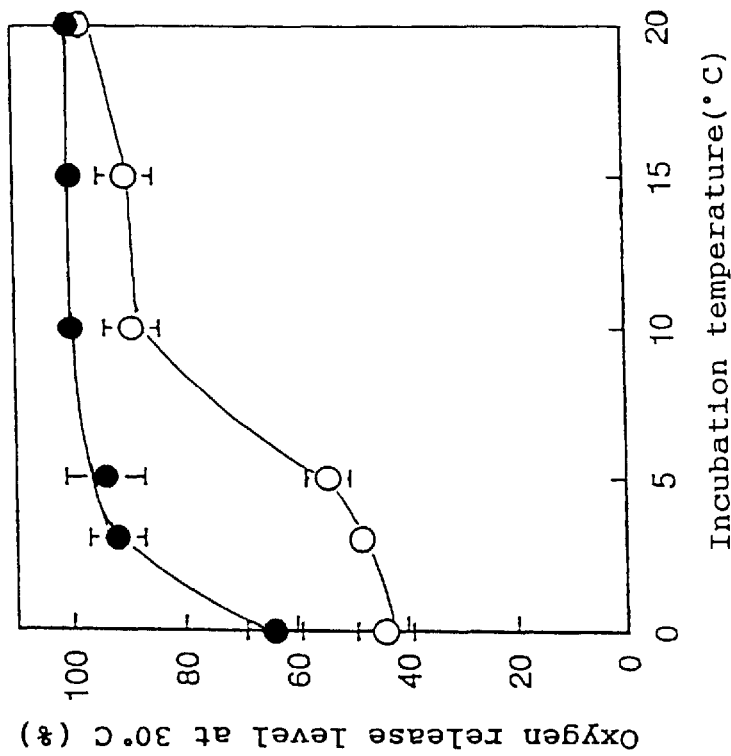
FIG. 6(A–B): Photosynthetic oxygen release level from the Synechococcus strains PCC7942 PAM (○) and PAMCOD (●) grown at low temperatures in the presence of 1 mM $NaHCO_3$ (A) or in the presence of 1,4-benzoquinone and 1 mM $K_3Fe(CN)_6$ (B).
Figure 6B:
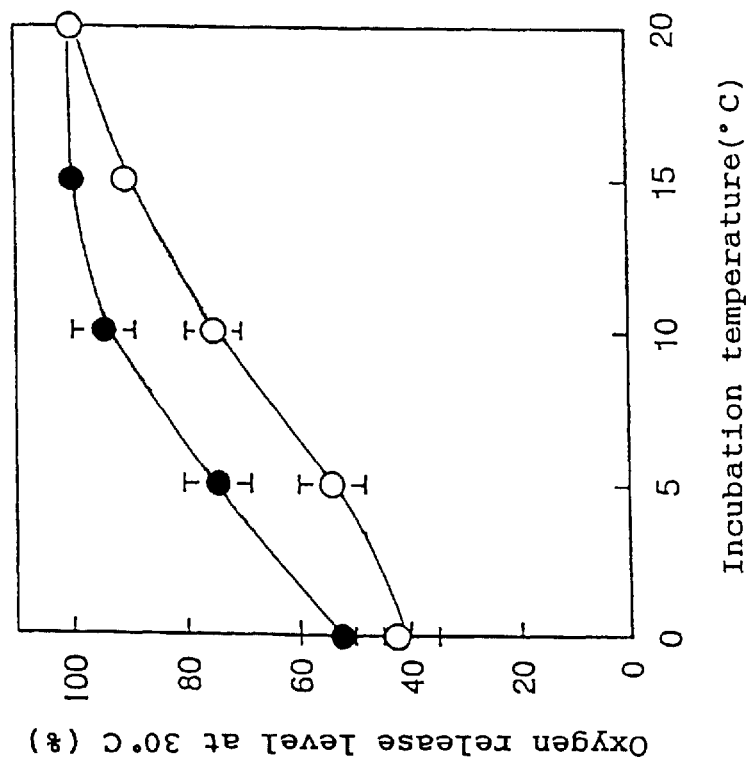

The results are shown in FIG. 6 (A: in the presence of $NaHCO_3$; B: in the presence of 1,4-benzoquinone and $K_3Fe(CN)_6$). As shown in FIG. 6A, the photosynthetic oxygen release activity of the strain PAMCOD was more tolerant to low temperatures than that of the strain PAM. As shown in FIG. 6B, the electron transport activity mediated by photochemical system II of the strain PAMCOD was also more tolerant to low temperatures than that of the strain PAM, i.e. the activity of the strain PAM decreased to 50% of the initial level at 5° C. while the activity of the strain PAMCOD remained almost at the initial level at 5° C. and began to decrease below 5° C.

Example 7

Preparation of a Binary Vector Plasmid Carrying the CodA Gene

A rbcS (ribulose 1,5-bisphosphate carboxylase small subunit) transit signal XbaI-NdeI fragment (about 200 bp)

from tobacco (Nicotiana sylvestris) was amplified by PCR using 5'CTGTCTAGATGTAATTAACAATGGCT3'(SEQ ID NO:3) and 5'CCACATATGCATGCATTGCACTCT3' (SEQ ID NO:4) as primers, and XbaI and NdeI sites were introduced.

Then, an N-terminal-BamHI fragment (about 100 bp) of the codA gene was amplified by PCR using 5'AACCATATGCACATCGACAACATC3'(SEQ ID NO:5) and 5'GCTCCATCCAGCGGTCCAGC3'(SEQ ID NO:6) as primers, then an NdeI site was introduced. A BamHI-SmaI fragment (about 1.6 kbp) of the codA gene was prepared by restriction enzymes. Finally, an SmaI-C-terminal fragment (about 80 bp) of the codA gene was amplified by PCR using 5'GAAACAGTCCTGCTTCCACAC3'(SEQ ID NO:7) and 5'GCGAGCTCTGCCTACACCGCCAT3'(SEQ ID NO:8) as primers, and an SacI site was introduced.

The GUS (β-glucuronidase) gene in the binary vector plasmid pBI221 was replaced by these fragments.

Figure 7:
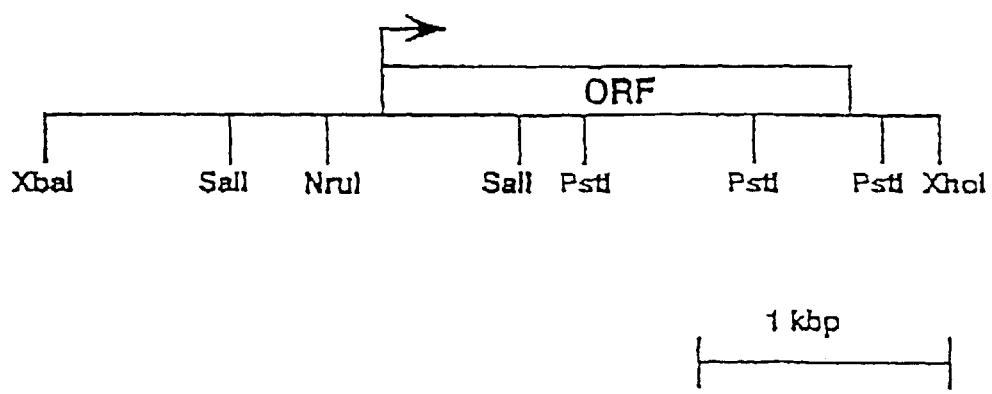
FIG. 7: Schematic representation showing the restriction enzyme map of the codA gene.

The restriction enzyme map of the codA gene is shown in FIG. 7.

Figure 8:
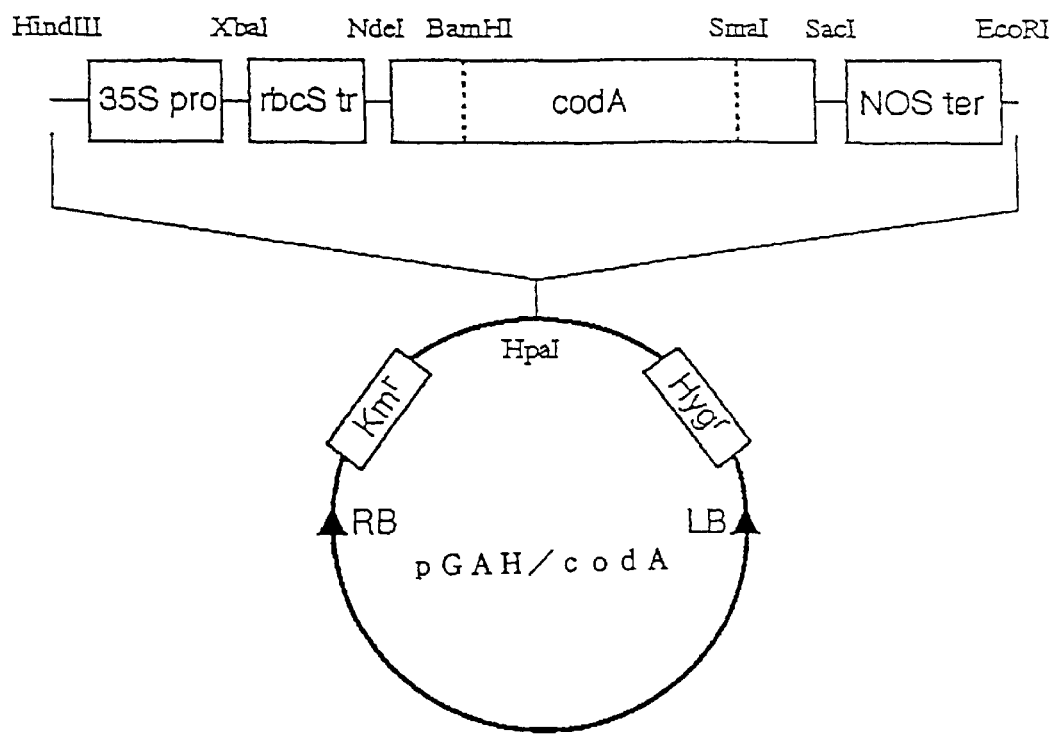
FIG. 8: Schematic representation showing the structure of the binary vector plasmid pGAH/codA used for transformation of Arabidopsis.

A HindIII-EcoRI fragment containing the cauliflower mosaic virus 35S promoter and the NOS (nopalin synthase) terminator was introduced into the binary vector plasmid pGAH to prepare a plasmid pGAH/codA (FIG. 8). This plasmid contains kanamycin- and hygromycin-resistant genes.

Example 8

Introduction of the Binary Vector Plasmid into Agrobacterium

The Agrobacterium tumefaciens EHA 101 bearing the Ti plasmid was mixed with the binary vector plasmid pGAH/codA obtained in Example 7, then frozen and melted, and screened on LB plates containing tetracycline and kanamycin. The resultant agrobacterium in which the codA gene had been integrated was designated as EHA101 (pGAH/codA).

Example 9

Transformation of Arabidopsis

The Arabidopsis thaliana strain WS was germinated to prepare a hypocotyl segment. This hypocotyl was callused in B5 medium (ICN Biochemicals) (pH 5.7) containing 0.05 mg/l of kinetin (Wako) and 0.5 mg/l of 2,4-D (Wako) to form hypocotyl calli.

Then, the calli were infected with the codA-containing Agrobacterium EHA101(pGAH/codA) prepared in Example 8 and cocultivated. After removal of Agrobacterium by B5 medium containing 250 mg/l of vancomycin, 500 mg/l of carbenicillin and 200 mg/l of Claforan, the cultures were transferred to a differentiation medium containing kanamycin and hygromycin (B5 medium containing 25 mg/l of kanamycin and 15 mg/l of hygromycin) to form shoots. Thus, kanamycin- and hygromycin-resistant shoots were selected to induce roots and to form seeds. The resultant T2 seeds are heterozygous individuals in which only one of the chromosomes has been transformed.

Then, the plants obtained from the T2 seeds were self-fertilized and selected by kanamycin and hygromycin to give homozygous T3 seeds.

The plants of the wild-type and transformant strains were used for experiments, after grown in a medium (pH 5.2) containing 0.1% HYPONEX (Hyponex Corporation, Marysville, Ohio, USA) at 22° C. for 30 days on water or soil consisting of vermiculite and perlite with illumination of 75 $\mu$mol $m^{-2}s^{-1}$ for 16 hours in a day and in the dark for the remaining 8 hours unless otherwise indicated.

Example 10

Immunological Study of the Expressed Choline Oxidase

An antibody to choline oxidase was prepared according to the method described in literature by the inventors of the present invention (Deshniumu, P. et al., Plant Mol. Biol. 29:897–907, 1995).

Leaves from 20-day old plants of the wild-type and transformant strains of Arabidopsis thaliana were ground in a microcentrifuge at 0C and the homogenates were centrifuged at 10,000×g for 10 minutes to prepare soluble fractions. Soluble proteins of the supernatant were separated by SDS-PAGE and transferred to a nylon membrane (Immobilon PVDF; Millipore, Bedford, Mass., USA). The membrane was incubated with the above antibody to choline oxidase and detected with a system consisting of a biotinylated secondary antibody, avidin and biotinylated horse radish peroxidase (ABC Kit; Vectastain, Burlingane, Calif., USA).

Figure 9:
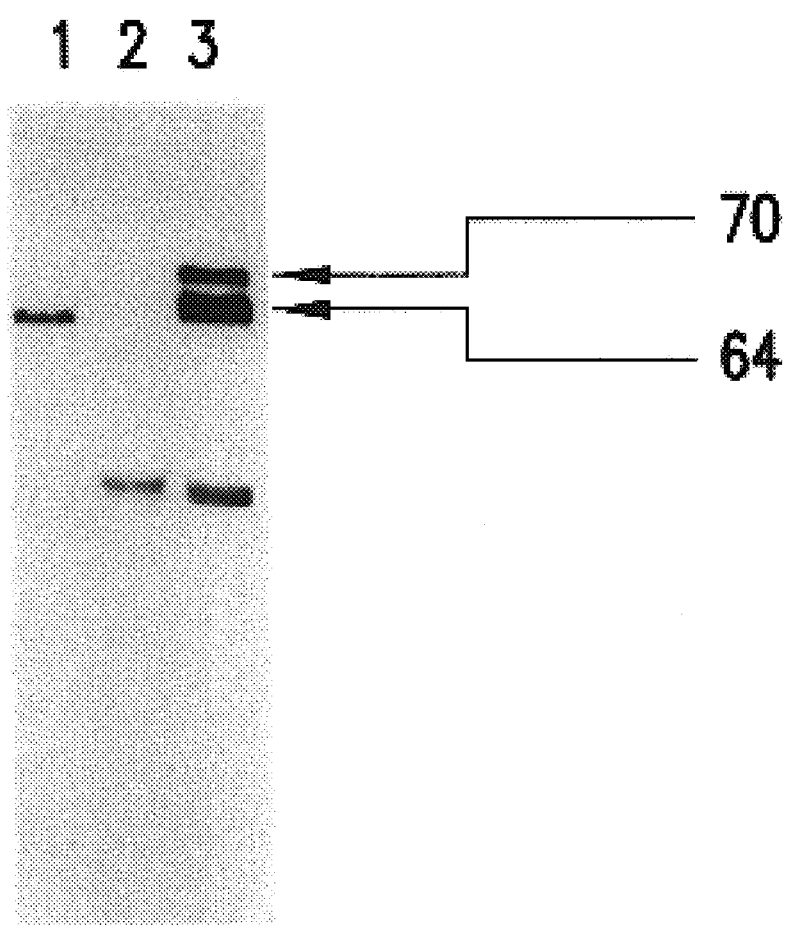
FIG. 9: Western blot analysis (photograph of electrophoresis) of choline oxidase in soluble fractions of the wild-type and transformed plants of Arabidopsis. Lane 1: choline oxidase derived from commercially available Arthrobacter globiformis (Sigma Chemical Co., St. Louis, Mo., USA); Lane 2: soluble fraction of the wild-type plant; Lane 3: soluble fraction of a transformed plant.

The results of Western blot analysis are shown in FIG. 9. The presence of an immunoresponsive protein of 64 kDa corresponding to choline oxidase was identified. A small amount of a protein of 70 kDa corresponding to a precursor of choline oxidase and the rbcS transit peptide were also observed. These results show that the codA gene was correctly integrated and expressed in chromosomes and that the expressed precursor was processed into a manure protein.

Then, localization of the expressed choline oxidase in plants was detected with the above antibody to choline oxidase by a method described in literature (Mustardy, L. et al., Plant Physiol. 94:334–340, 1990). A small piece of young leaf from a plant was fixed with 1% glutaraldehyde in 0.1 M sodium phosphate buffer (pH 7.2) for one hour. After rinsed with the same buffer, the sample was dehydrated with ethanol and placed in Lowicryl K4M resin (TAAB Laboratories Equipment Ltd., Berkshire, U.K.). Immuno-gold labeling was done by a method described in literature (Mustardy et al., supra).

As a result, the expressed choline oxidase was observed to be localized in stroma of chloroplasts, indicating that choline oxidase had been transported to chloroplasts.

Example 11

Determination of Betaine and Chlorophyll Levels in Transformed Plants

Betaine content in leaf of plants was calculated by measuring NMR spectra of a quaternary ammonium compound (Wall, J. et al., Analyt. Chem. 32:870–874, 1960). 5 g of leaf of the wild-type and transformed plants were powdered in liquid nitrogen by a ceramic motor. This powder was suspended in 25 ml of 1.0 M $H_2SO_4$ and incubated at 25° C. for 2 hours. After unsoluble matters were removed, the supernatant was recovered by centrifugation at 1000×g for 10 minutes. The supernatant was incubated with 10 ml of a $KI-I_2$ solution at 0° C. for 2 hours. Betaine and choline modified with periodide were recovered by centrifugation at 1000×g for 30 minutes and dissolved in 0.5 ml of $CD_4OH$ (Wako) containing 0.5 mM 2-methyl-2-propanol (Wako) as an internal standard to measure $^1H$ NMR spectra. Two main peaks corresponding to betaine and choline were observed, and the integrated betaine peaks were used for determination of the concentration.

Chlorophyll content in leaf was measured by the following procedure. Leaf (1 g) was powdered in liquid nitrogen by a ceramic motor. The powder was suspended in 10 ml of acetone : water (4:1, v/v). After incubation for 30 minutes, unsoluble matters were removed and the supernatant was subjected to spectrophotometry (Arnon, D. I. Plant Physiol. 24:1–15, 1949).

As a result, both of betaine and choline were observed in the transformed plant, while only choline was observed in the wild-type plant. Betaine content was 1.0 $\mu$mol/g fresh leaf. Chlorophyll content was 0.3 $\mu$mol/g fresh leaf.

Example 12

Tolerance of Transformed Arabidopsis to Low-temperature Stress

A test was performed to determine whether or not the introduction of the codA gene and accumulation of betaine confer tolerance on low-temperatures stress.

The wild-type and transformed plants were incubated at 5° C. for 7 days under continuous illumination of 250 $\mu$mol $m^{-2}s^{-1}$. No significant difference was observed with the naked eye between the wild-type and transformed plants. When these plants were incubated at 22° C. for further 2 days, leaves of the wild-type plant began to droop and whiten. However, the transformed plant was not apparently affected at all by this treatment.

Example 13

Inactivation of Photochemical System II Activity at Low Temperatures

Influences of low-temperature stress on photochemical system II activity of leaf of the transformed plant were assessed by monitoring fluorescence of chlorophyll. Activity of photochemical system II was measured as a ratio of variable chlorophyll fluorescence to maximum chlorophyll fluorescence (Fv/Fm) by using a pulse intensity-modulated fluorometer (PAM-2000; Walts, Effeltrich, Germany) (Annu. Rev. Plant Physiol. Plant Mol. Biol. 42:313–349, 1991).

Figure 10:
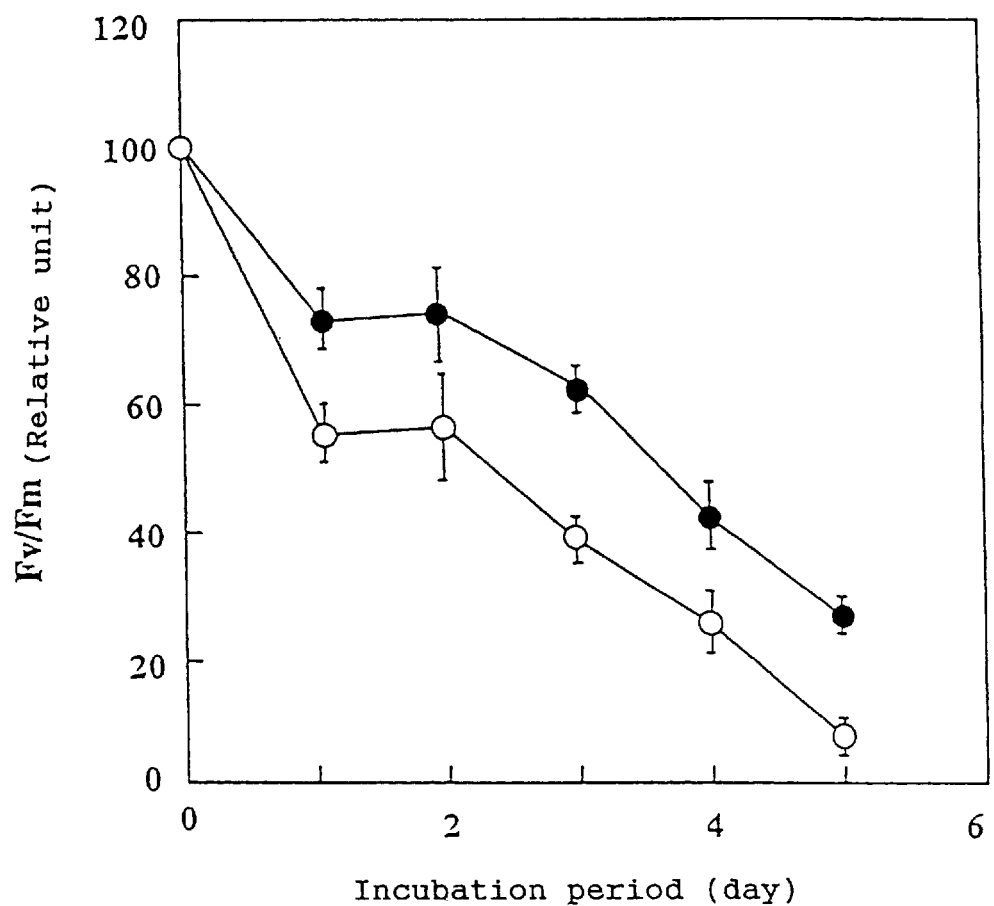
FIG. 10: Influence of low temperature on photochemical system II in leaves of the wild-type and transformed plants of Arabidopsis. (○): wild-type plant; (●): transformed plant.

The results are shown in FIG. 10. After incubation at 5° C. for 7 days under continuous illumination of 250 $\mu$mol $m^{-2}s^{-1}$, photosynthetic system II activity decreased in both of the wild-type and transformed plants. Decline was sharp on the first day and then slowed down in both of the wild-type and transformed plants. However, the transformed plant showed much slower inactivation than the wild-type plant at every instant. After incubation for 5 days, the wild-type plant almost completely lost activity, but the transformed plant kept about 30% of the original level of activity. However, no significant difference was observed in photosynthetic system II activity between them at 10 to 15° C.

Example 14

Figure 11:
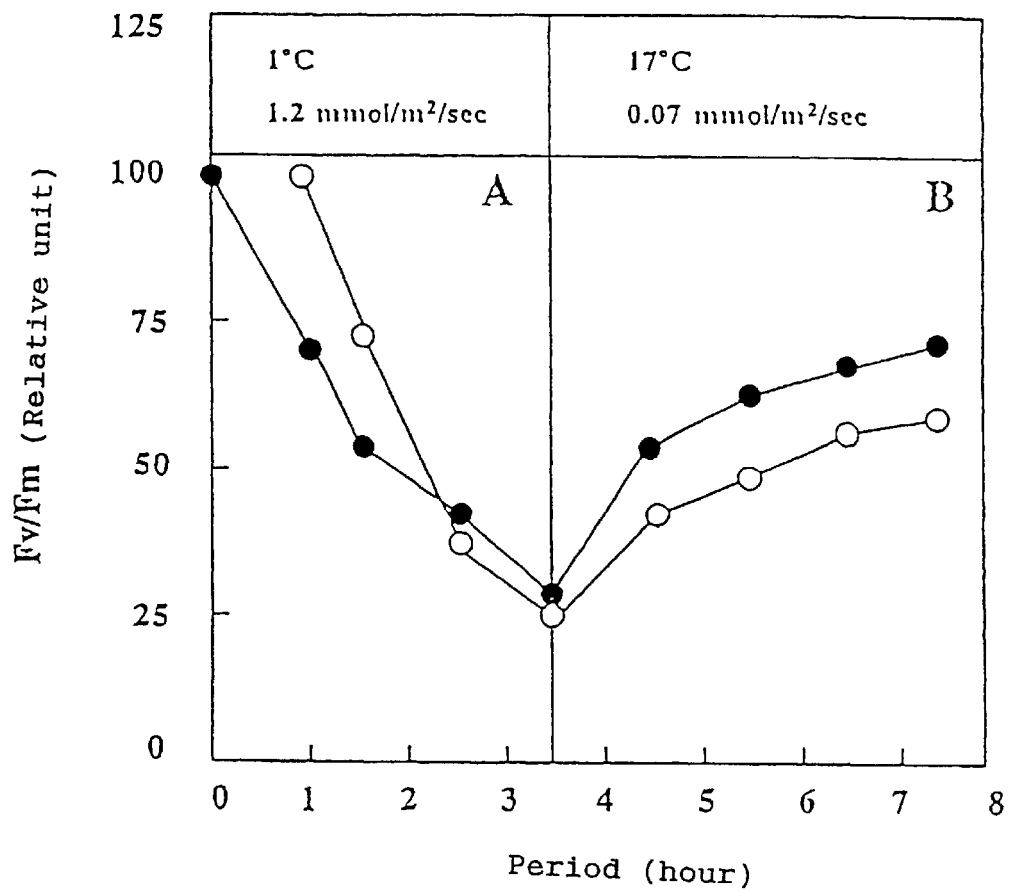
FIG. 11: Inhibition of photosynthesis at low temperature (A) and recovery from inhibition of photosynthesis at low temperature (B) in leaves of the wild-type and transformed plants of Arabidopsis. (○): wild-type plant; (●): transformed plant.

Inhibition of Photosynthesis by Low Temperatures and its Recovery, as Well as Freeze Resistance
(1) Tests on Inhibition of Photosynthesis by Low Temperatures and Recovery from the Inhibition of Photosynthesis The extent of inhibition of photosynthesis was measured at a temperature as low as 1° C. The results are shown in FIG. 11A. Leaves of the transformed plant were more tolerant to inhibition of photosynthesis by low temperatures than leaves of the wild-type plant. Namely, leaves of the wild-type plant lost about 75% of photosynthetic system II activity after 2.5 hours, while it took 3.5 hours or more until leaves of the transformed plant were inactivated to the same extent.

Figure 12:
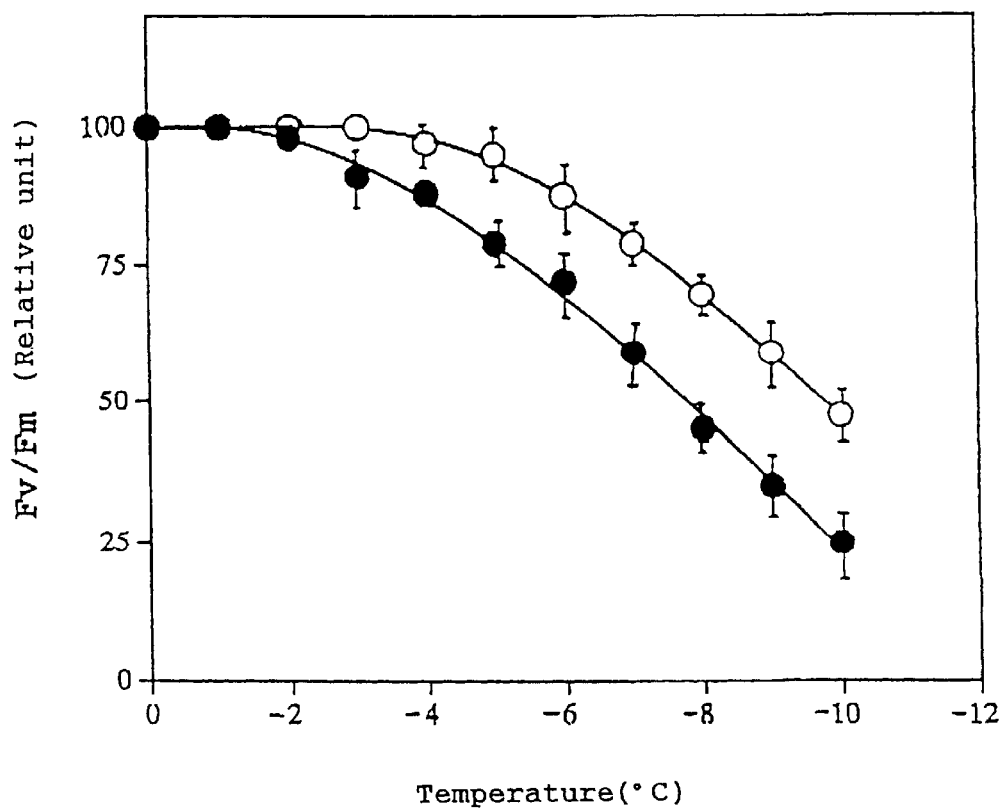
FIG. 12: Results of freeze resistance tests on leaves of the wild-type and transformed plants of Arabidopsis. (○): wild-type plant; (●): transformed plant.

FIG. 11B shows results of recovery test from photosynthesis inhibition by low temperatures. After the above low-temperature test, leaves were incubated at 17° C. with 70 $\mu$mol $m^{-2}s^{-1}$. Leaves of both of the wild-type and transformed plants showed recovery from photosynthesis inhibition by low temperatures. However, the transformed plant showed a higher extent of recovery than the wild-type plant. After incubation for 4 hours, leaves of the wild-type plant recovered 25 to 50% of the original activity. However, leaves of the transformed plant showed recovery of 25 to 75%.
(2) Freeze Resistance Tests On Leaves Leaves of the wild-type and transformed plants of Arabidopsis were torn and immersed in water at a temperature decreasing at a rate of 3° C./min. When the temperature was lowered to −3° C., a needle cooled by liquid nitrogen was applied to leaves to freeze them. Then, leaves were cooled at a rate of 1C/hour to various measuring temperature ranging from −2° C. to −12° C. The leaves were removed and allowed to stand overnight at 4° C. so that they melted. On the following day, the temperature was returned to room temperature and photochemical system II activity was measured. The results are shown in FIG. 12. At any temperature, the transformed plant showed higher activity than the wild-type plant.

Example 15

Influences of Low-temperature Treatment at the Water-absorption Stage on Germination of Seeds Seeds of: the wild-type plant and T3 seeds of the transformed plant were maintained in ice water (about 0° C.) for 2 hours and sterilized, then germinated on MS (Murashige-Skoog) medium containing 2% sucrose and 0.5% gellan gum. Seeds were germinated at 22° C. for 20 days with light for 16 hours and in the dark for 8 hours each day.

Figure 13A:
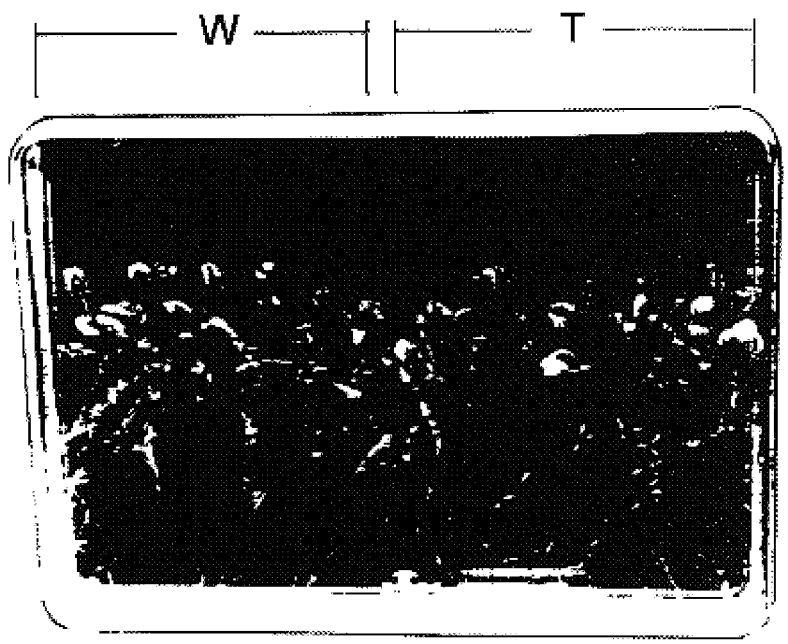
FIG. 13: Influence of low temperature at water absorption stage on germination of seeds of the wild-type and transformed plants of Arabidopsis (photographs showing morphology of the organisms). A: seeds germinated without low-temperature treatment at water absorption stage; B: seeds germinated after low-temperature treatment at water absorption stage. In both of A and B, W on the left shows the results from seeds of the wild-type plant and T on the right shows the results from seeds of the transformed plant.
Figure 13B:
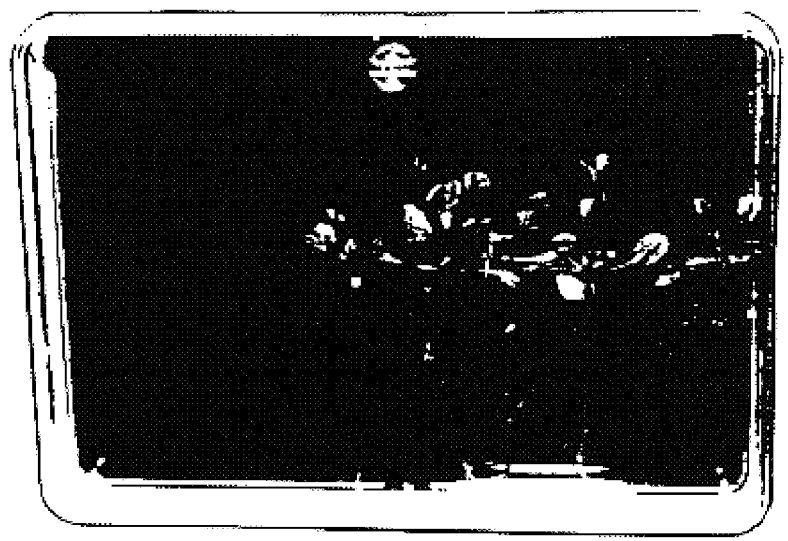

The results are shown in FIG. 13. As apparent from the figure, both of the wild-type and transformed plants germinated when their seeds were not subjected to cooling treatment at the water-absorption stage (FIG. 13A). When the seeds were subjected to cooling treatment at the water-absorption stage, the wild-type plant did not germinate, but the transformed plant germinated and grew equally to untreated seeds (FIG. 13B).

Example 16

Preparation of a Chimeric CodA Gene Used for Transformation of Rice

Figure 14:
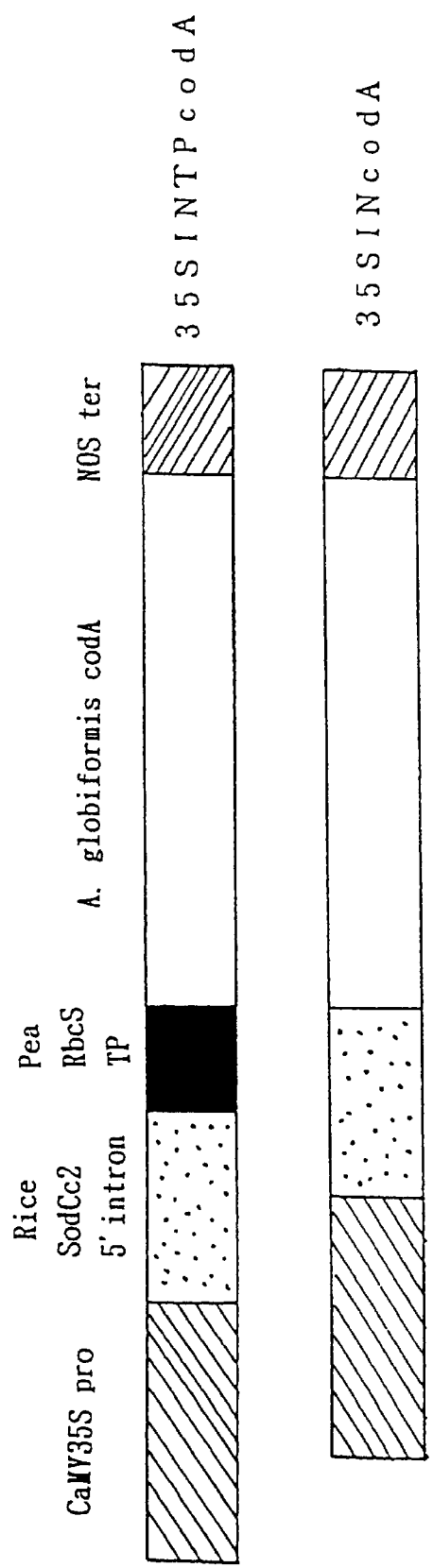
FIG. 14: Structures of two chimeric codA genes used for transformation of rice, i.e. 35SINTPcodA and 35SINcodA.

Two chimeric codA genes (designated as 35SINcodA and 35SINTPcodA, respectively) which are localized in cytosol or plastid after translation of the choline oxidase gene (codA) derived from Arthrobacter globiformis under transcriptional-control of the cauliflower mosaic virus 35S promoter were prepared on the plasmid pUC119 by the procedure described in Example 6 (see FIG. 14). Considering that the presence of an intron is required for high expression of a gene in rice (for example, see Tanaka, A. et al., Nucleic Acids Res. 18:6767–6770, 1990), an intron in the 5' non-translated sequence of the superoxide dismutase gene of rice (SodCc2: Sakamoto, A. et al., FEBS Lett. 358:62–66, 1995) was introduced into both chimeric genes. Further, a DNA sequence derived from the rbcS transit peptide (Coruzz, G. et al., EMBO J 3:1671–1679, 1984) from pea was added to 35SINTPcodA, in order to transfer the codA protein to chloroplasts.

Example 17

Transformation of Rice

Each of the two chimeric codA genes prepared in Example 16 was introduced into suspension culture cells from scutellum calli of rice seeds together with the selection marker hygromycin-resistant gene by a particle gun device. The transformed calli were selected based on the antibiotic resistance and redifferentiated into plants. Polymerase Chain Reaction (PCR) was run on the transformed calli or transformed/redifferentiated individuals showing hygromycin resistance, to assess integration and transcription of the codA gene into the nuclear genome by Northern blot technique and select 80 to 100 or more transformants for each codA gene.

Example 18

Analysis of Expression of the CodA Gene in Transformed Rice

The transformants obtained in Example 17 were screened by Western blot technique to obtain the transformed rice (the present generation) expressing the codA gene at the protein level, finally including 6 individuals carrying the gene localized in plastid and 10 individuals carrying the gene localized in cytosol.

Rice lacks endogenous choline oxidase activity, but soluble fractions prepared from leaves or roots of the transformants showed choline oxidase activity. Contrary to expectation, all the individuals of the plastid-type transformants were found to express a lower amount of choline oxidase protein than the cytosol-type, despite of the same expression promoter used.

When the expression of the codA gene was further examined by Northern blot technique, any significant difference was not found in the amount of both genes expressed at the transcription level. When processing of the intron was examined by reverse transcriptive PCR, a plurality of splicing variants containing different 3'-acceptor sites which may not bring about normal translation into protein were detected from the mRNA transcribed from the plastid-type gene. This suggested that the low level protein expression by the plant transformed with the plastid-type gene might be due to abnormal processing of the mRNA precursor. This phenomenon seems to be related to the fact that the sequence encoding the transit peptide used for plastid-targeting of choline oxidase was derived from a dicotyledon (pea rbcs gene). Therefore, it may be readily expected that the expression of the codA in rice chloroplasts would be more efficient and the resultant transformed rice would be more tolerant to temperature stress if the sequence encoding the transit peptide was derived from a monocotyledon such as rice rbcs.

Example 19

Betaine Biosynthesis in Transformed Rice

Figure 15:
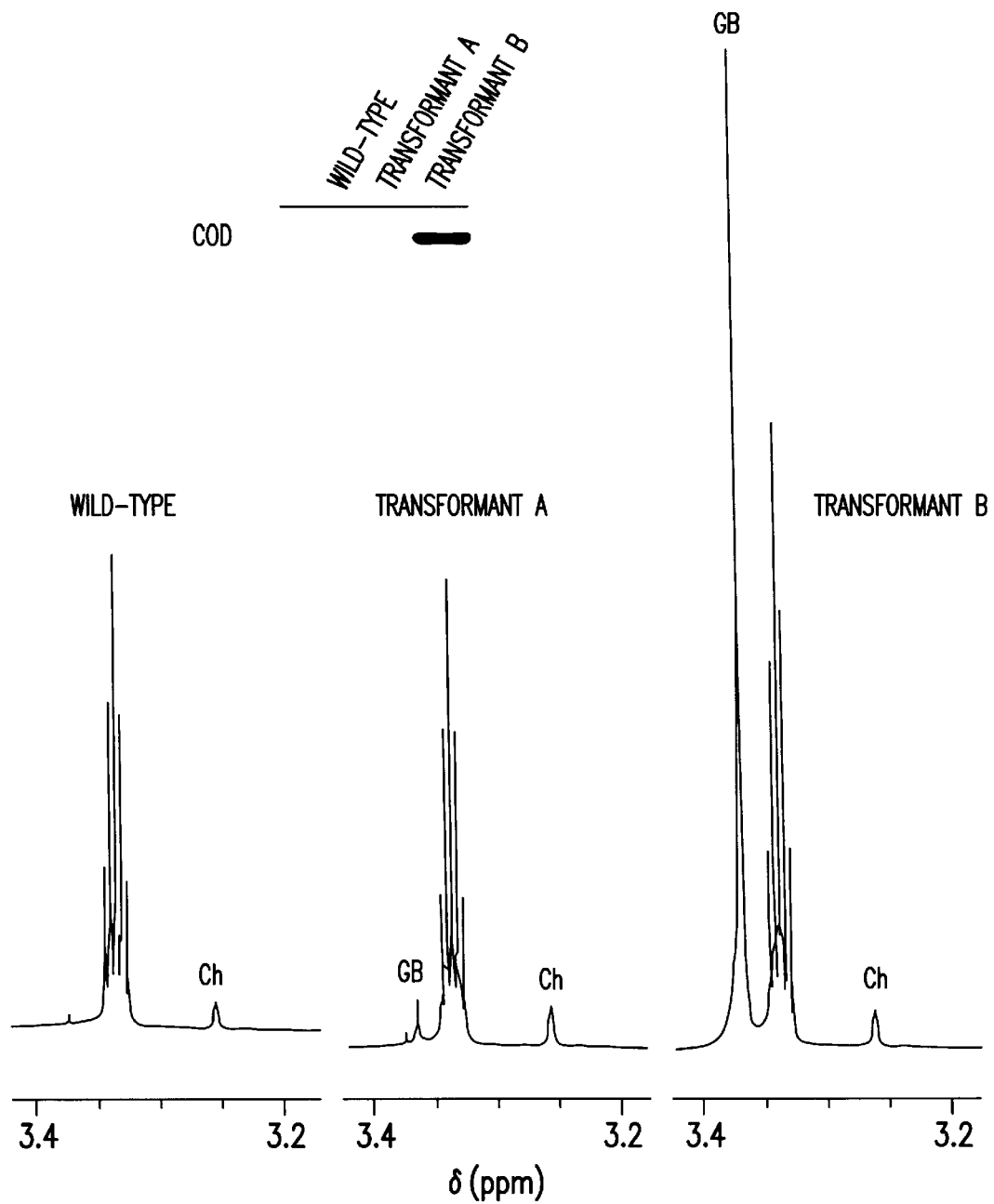
FIG. 15: NMR charts representing betaine accumulation in rice plants of the wild-type strain, a transformant (A) which does not express the codA gene, and a transformant (B) which expresses the codA gene. In the figure, GB and Ch represent peaks corresponding to betaine and choline, respectively.

Betaine accumulating in tissues of transformants expressing choline oxidase was detected by proton NMR. FIG. 15 shows the results of the NMR of the wild-type strain, a transformant which does not express the codA gene (FIG. 15A) and a transformant which expresses the codA gene (FIG. 15B).

The transformant which expresses choline oxidase biosynthesized betaine and the accumulating amount of betaine showed a positive correlation with the amount of choline oxidase detected by Western blot technique. The accumulating amount of betaine was greater in leaves than in roots and reached 4 $\mu$mol/g fresh leaf in individuals highly expressing the codA gene. This is the first case in which rice gained betaine-synthesizing ability through a genetic engineering technique.

Example 20

Inactivation of Photosynthesis Under Illumination at Low Temperatures

In order to examine whether transformed plants gained temperature tolerance by the presence of betaine or other causes, the following tests were performed using the transformant prepared by transforming the Synechococcus PCC7942 with a plasmid containing the codA gene and PAM prepared by transforming it with pAM1044 alone in Example 1.

Figure 16A:
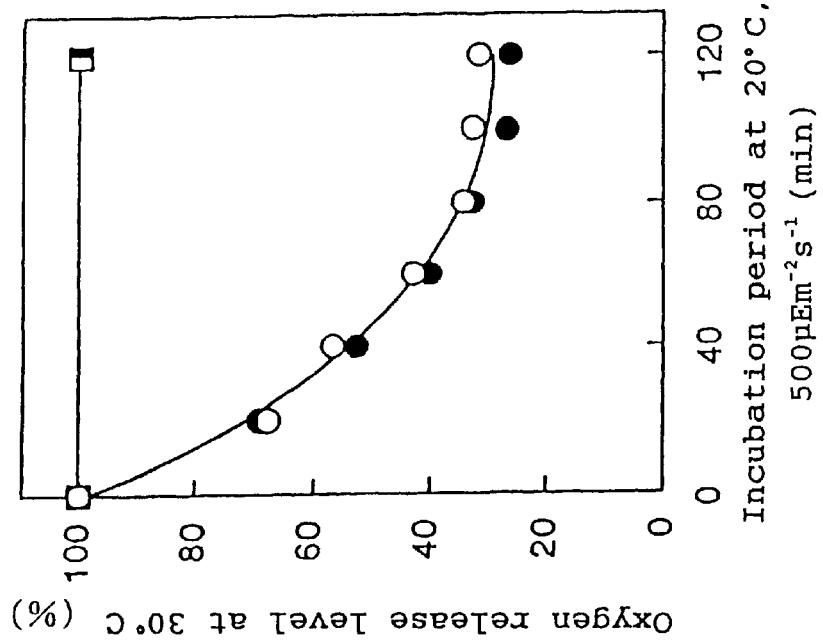
FIG. 16(A–B): Effect of the introduction of the codA gene into Synechococcus PCC7942 on electron transport mediated by photochemical system II in terms of relative values vs. maximum activation assumed as 100%. (○): PAM cells under illumination; (●): PAMCOD cells under illumination; (□): PAM cells in the dark; (■): PAMCOD cells in the dark.

PAM and PAMCOD cells preliminarily grown at 30° C. in the presence of 1 mM choline chloride were grown at 20° C. under illumination or dark conditions. Under dark conditions, activity of photochemical system II was maintained. However, activity of photochemical system II of PAM cells decreased to 35% of the original level after cultivation with 500 $\mu$Em$^{-2}$s$^{-1}$ for 120 minutes (FIG. 16A). Activity of photochemical system II of PAMCOD cells also decreased but to a lesser extent than PAM cells (FIG. 16A). This revealed that photochemical system II of PAMCOD cells is more tolerant to photoinhibition than that of PAM cells.

Figure 16B:
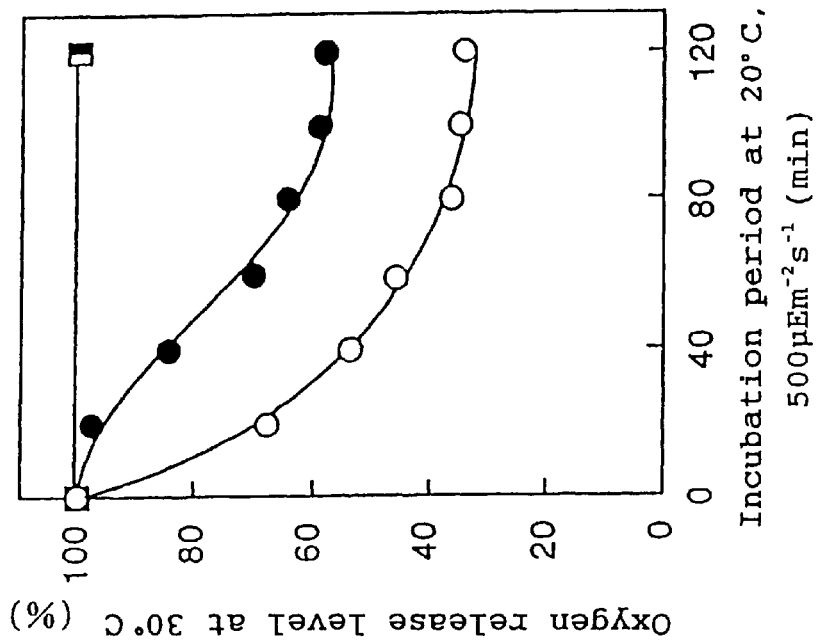

Photoinhibition of photochemical system II is caused by competition between light-induced inactivation of D1 protein and recovery of photochemical system II by uptake of D1 protein newly synthesized (Aro, E.-M. et al., Biochim. Biophys. Acta 1019:269–275, 1990; Aro, E.-M. et al., Biochim. Biophys. Acta 1143:113–134, 1993). In order to examine whether the tolerance of PAMCOD cells to photostress at low temperatures results from suppression of inactivation of D1 protein or promotion of D1 protein synthesis, photoinhibition was induced in the presence of a protein synthesis inhibitor, linomycin (400 mg/ml). Under dark conditions, linomycin had no influence on photochemical system II activity of PAM and PAMCOD cells. Under illumination, photochemical system II complexes were inactivated at the same speed in cells of both transformants (FIG. 16B). This result shows that the improvement of tolerance of PAMCOD cells to photostress at low temperatures does not result from suppression of inactivation of D1 protein. The presence of betaine seemed to promote recovery of photochemical system II.

Example 21

Recovery From Photoinhibition

PAM and PAMCOD cells were tested for recovery of photochemical system II from photoinhibition by measuring oxygen release activity. Cells were exposed to light of 3500 $\mu$Em$^{-2}$s$^{-1}$ to inhibit photochemical system II complexes to 15% of the original level. Then, cells were grown at 20° C.

or 30° C. under illumination of 70 μEm$^{-2}$s$^{-1}$. The results are shown in FIG. 17.

Figure 17B:
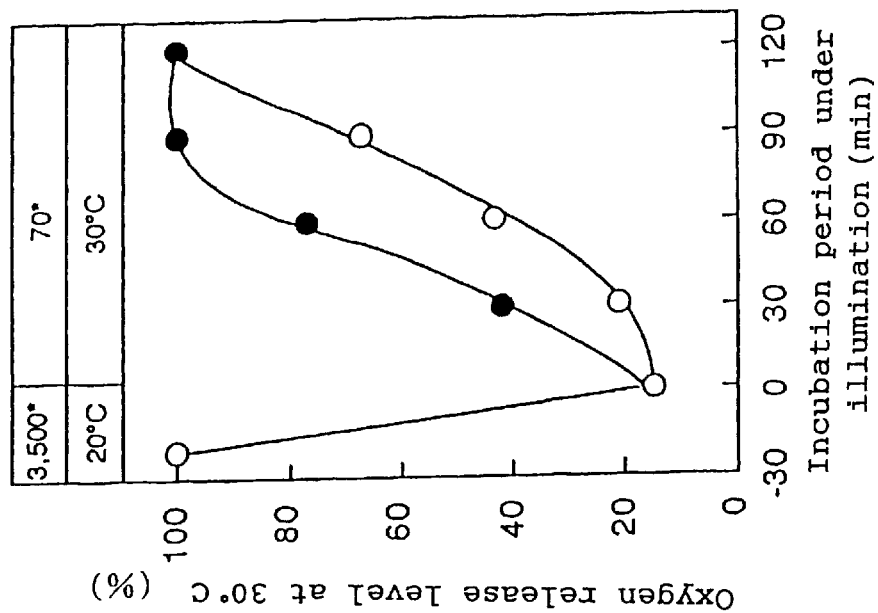
FIG. 17(A–B): Recovery of electron transport mediated by photochemical system II from photoinhibition at low temperature when the codA gene was introduced into Synechococcus PCC7942. (○): PAM cells under illumination; (●): PAMCOD cells under illumination.
Figure 17A:
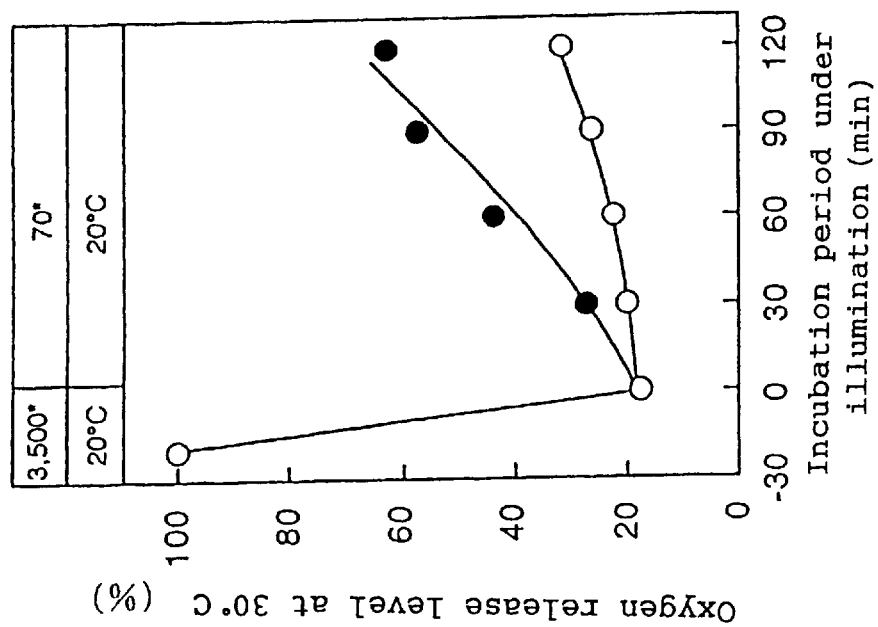

At 20° C., PAM cells showed only slight recovery of photochemical system II complexes from photoinhibition. However, PAMCOD cells recovered to 60% of the original level after 2 hours (FIG. 17A). At 30° C., cells of both strains completely recovered activity of photochemical system II after 2 hours. However, PAMCOD cells recovered much faster than than PAM cells (FIG. 17B).

Example 22

Inactivation of Photosynthesis Under Dark Conditions at Low Temperatures

Figure 18B:
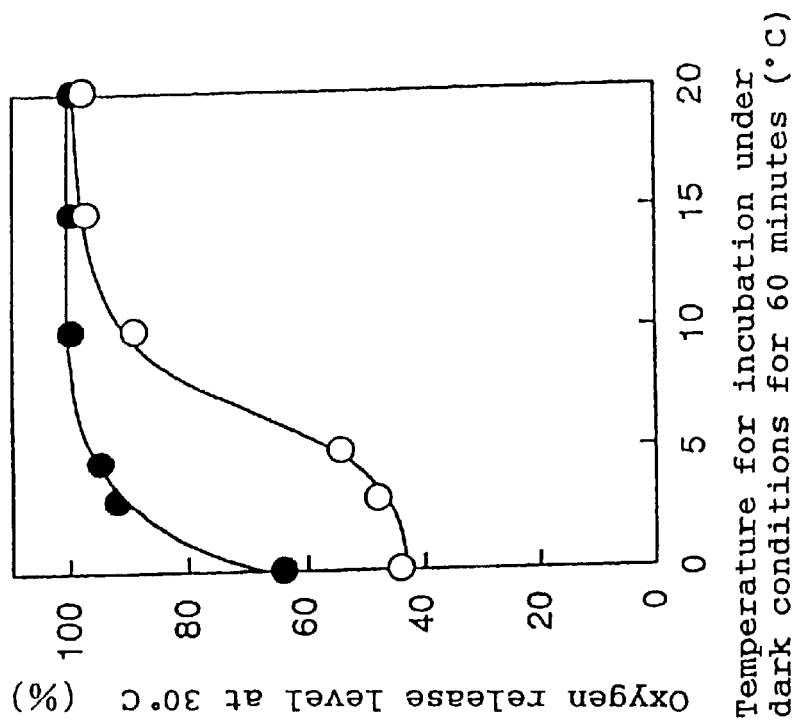
FIG. 18(A–B): Effect of low-temperature treatment under dark conditions on photosynthetic oxygen release when the codA gene was introduced into Synechococcus PCC7942. (○): PAM cells under illumination; (●): PAMCOD cells under illumination.
Figure 18A:
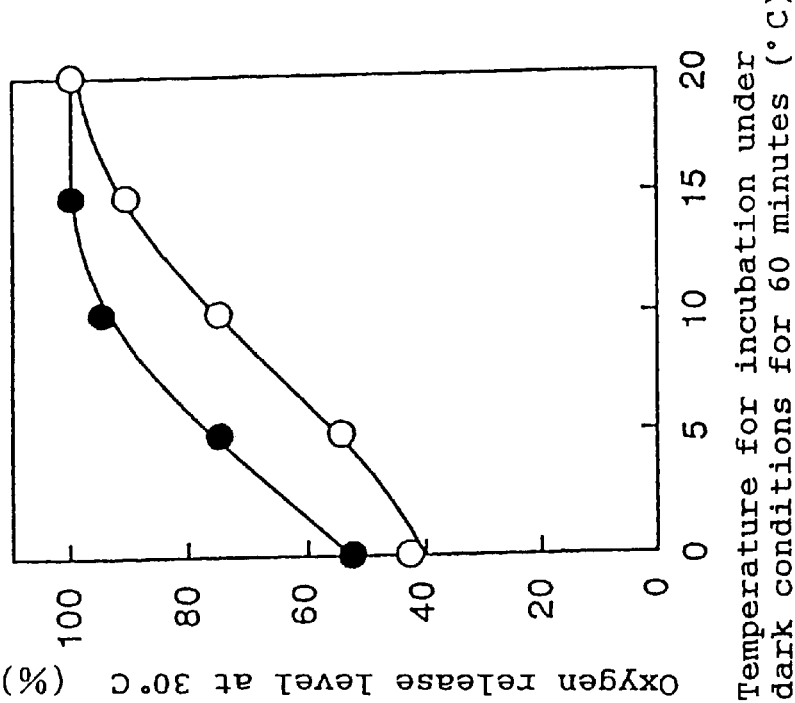

Tolerances of PAM and PAMCOD cells to low-temperature stress were compared under dark conditions at low temperatures. Effects of various low-temperature treatments on inactivation of net photosynthesis and electron transport mediated by photochemical system II in both cells are shown in FIG. 18. Oxygen release activity by photosynthesis of PAMCOD cells was more tolerant to low temperatures than that of PAM cells (FIG. 18A). Similar results were obtained for electron transport mediated by photochemical system II. The activity of PAM cells decreased to 50% of the original level at 5° C., while the activity of PAMCOD cells remained almost at the same level as that of the control at 5° C. and decreased below 5° C. (FIG. 18B). These results show that photosynthesis of PAMCOD cells is more tolerant to low temperatures than that of PAM cells.

Example 23

Phase Transition of Protoplasmic Membranes

Cyanobacterial cells exposed to low temperatures have been reported to lessen growth or photosynthetic activity because of change of the lipid phase of protoplasmic membranes from liquid crystal state into phase separation state (Murata, N., J. Bioenerg. Biomembr. 21:61–75, 1989). A test was performed to examine whether or not the improvement of low-temperature tolerance of PAMCOD cells is related to the change of the lipid phase of membranes.

Figure 19:
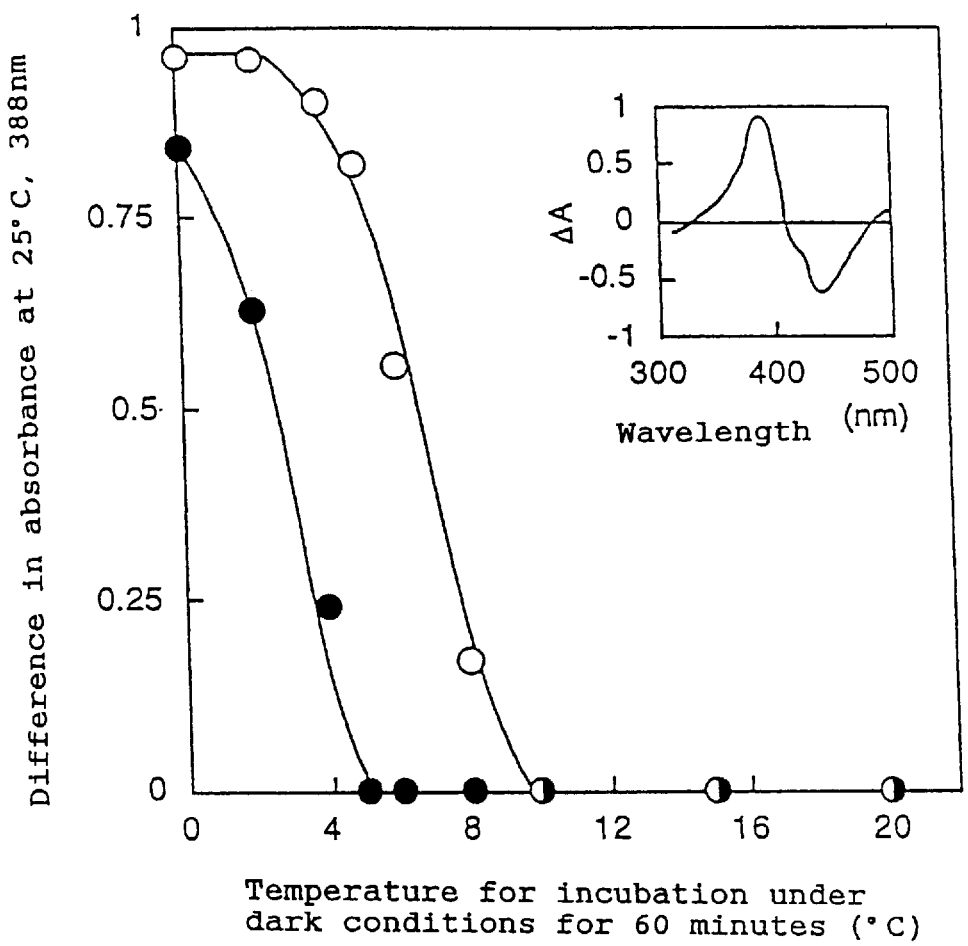
FIG. 19: Effect of low-temperature treatment on lipid phase transition when the codA gene was introduced into Synechococcus PCC7942. (○): PAM cells under illumination; (●): PAMCOD cells under illumination.

Transition of the lipid phase of protoplasmic membranes can be tested by agglutination of zeaxanthin by monitoring change of absorbance in cells of Synechococcus PCC7942 and PCC6301 (previously called as Anacystis nidulans) at 388 nm (Brand, J. J., Plant Physiol. 59:970–973, 1977; Gombos, Z. et al., Plant Physiol. 80:415–419, 1986; Murata N., J. Bioenerg. Biomembr. 21:61–75, 1989; Ono, T. et al., Plant Physiol. 67:176–181, 1981; Wada, H. et al., Nature 347:200–203, 1990; Yamamoto, H. Y. et al., Biochim. Biophys. Acata 507:119–127, 1978). FIG. 19 shows the results from PAM cells and PAMCOD cells tested by a similar method. FIG. 19 shows that phase transition of membrane lipid of PAM cells appears at 10° C. and terminates at 2° C., with the intermediate temperature being 6° C. On the other hand, transition of membrane lipid of PAMCOD cells starts at 5° C. This means that lipid transition of protoplamic membranes of PAMCOD cells occurs at a temperature 5° C. lower than PAM cells.

Example 24

Change of Membrane Lipid and Protein

Transition temperature of membrane lipid of cyanobacteria has been known to depend on the extent of unsaturation of fatty acid and the nature of lipid (Murata, N., J. Bioenerg. Biomembr. 21:61–75, 1989). Thus, membrane lipid of PAMCOD cells was tested. Tables 1 and 2 show components of the fatty acid and glycerolipid in protoplasmic membranes and thylakoid membranes of PAM and PAMCOD cells. Table 1 shows lipid composition in cells grown at 30° C. in the presence of 1 mM choline chloride. Table 2 shows glycerolipid composition in cells grown at 30° C. in the presence of 1 mM choline chloride.

TABLE 1

| | Fatty acid | | | | | | |
|---|---|---|---|---|---|---|---|
| | 14:0 | 14:1 | 16:0 | 16:1 | 18:0 | 18:1(9) | 18:1(11) |
| | (mole %) | | | | | | |
| Protoplasmic membrane | | | | | | | |
| PAM | 1 | 1 | 54 | 36 | 3 | 2 | 2 |
| PAMCOD | 2 | 2 | 53 | 38 | 2 | 2 | 2 |
| Thylakoid membrane | | | | | | | |
| PAM | 1 | 2 | 52 | 40 | 2 | 2 | 2 |
| PAMCOD | 1 | 2 | 50 | 40 | 2 | 2 | 2 |

Abbreviation:
14:0: myristic acid
14:1: Δ9-myristic acid
16:0: palmitic acid
16:1: Δ9-palmitic acid
18:0: stearic acid
18:1(9): Δ9-stearic acid
18:1(11): Δ11-stearic acid All the double bonds are in cis-form.

TABLE 2

| | Tylakoid membrane | | Protoplasmic membrane | |
|---|---|---|---|---|
| Lipid class | PAM (mole %) | PAMCOD (mole %) | PAM (mole %) | PAMCOD (mole %) |
| MGDG | 54 | 53 | 56 | 55 |
| DGDG | 22 | 23 | 19 | 19 |
| SQDG | 14 | 14 | 15 | 15 |
| PG | 10 | 10 | 10 | 11 |

Abbreviation:
MGDG: monogalactosyl diacylglycerol
DGDG: digalactosyl diacylglycerol
SQDG: sulfoquinovosyl diacylglycerol
PG: phosphatidylglycerol As is apparent from Tables 1 and 2, no significant difference was observed between both.

Figure 20:
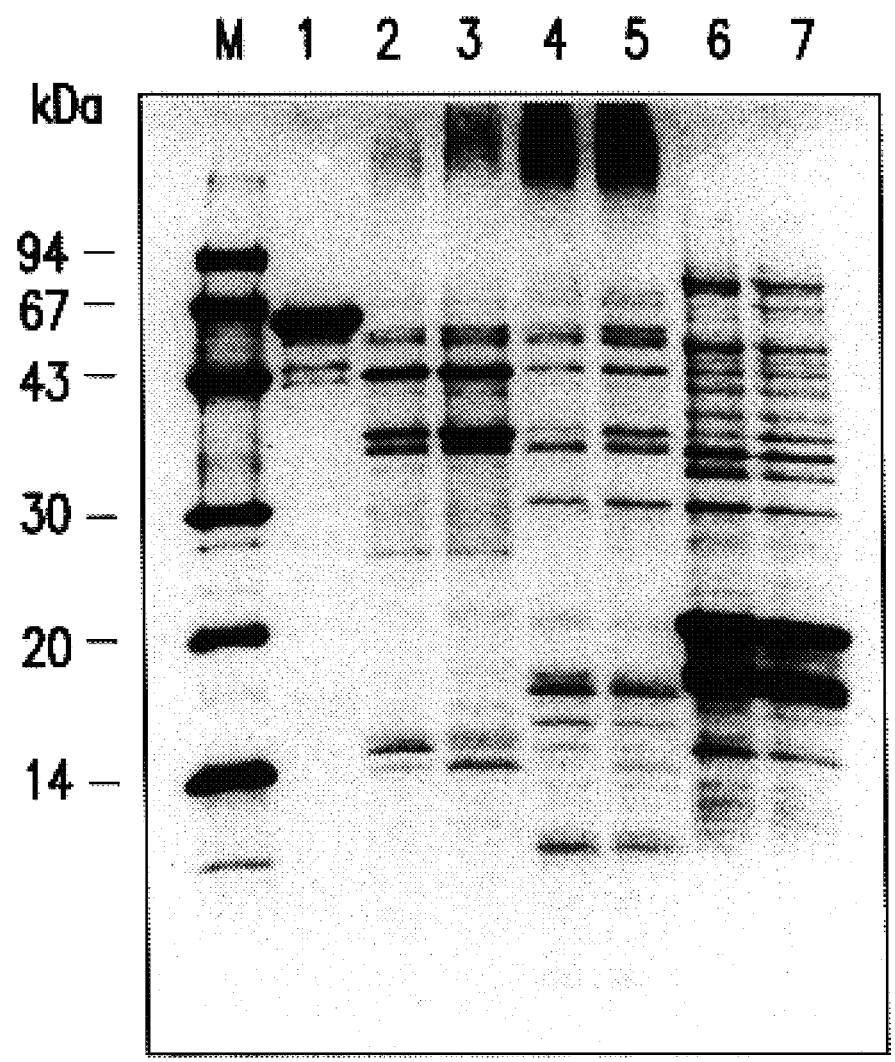
FIG. 20: Electrophoretogram showing changes of protein in the soluble fractions and membrane fractions when the codA gene was introduced into Synechococcus PCC7942. Lane 1: choline oxidase; 2: protoplasmic membrane of PAM cells; 3: protoplasmic membrane of PAMCOD cells; 4: thylakoid membrane of PAM cells; 5: thylakoid membrane of PAMCOD cells; 6: soluble fraction of PAM cells; 7: soluble fraction of PAMCOD cells. An arrow indicates choline oxidase.

FIG. 20 shows electrophoretic patterns of proteins of membrane and soluble fractions of PAM and PAMCOD cells. A slight difference was observed in membrane fractions. Namely, PAMCOD cells showed an increase in amount of the protein of 14 kda and a decrease in amount of the protein of 16 kda. No other difference was found in soluble fractions except that PAMCOD cells showed a band corresponding to choline oxidase.

Thus, there was found no significant difference in membrane lipid or protein between PAM and PAMCOD cells, indicating that the protection of photochemical system II as seen in PAMCOD cells at low temperatures is an effect of betaine.

What is claimed is:

1. A method for producing a temperature-tolerant higher plant, which comprises transforming a higher plant with a recombinant vector carrying a gene encoding choline oxidase,
    wherein said gene encoding choline oxidase comprises a nucleotide sequence encoding the amino acid sequence of SEQ ID NO:2; and
    wherein temperature-tolerant is defined as the ability to grow at higher or lower temperatures than the temperatures which normally allow non-transformed plants of the same species to grow.

2. The method of claim 1 wherein the gene encoding choline oxidase is derived from the soil bacteria Arthrobacter.

3. The method of claim 1 wherein the higher plant is a dicotyledon.

4. The method of claim 3 wherein the dicotyledon is a brassicaceous plant.

5. The method of claim 1 wherein the higher plant is a monocotyledon.

6. The method of claim 5 wherein the monocotyledon is a gramineous plant.

7. A temperature-tolerant plant produced by the method of claim 1, or a progeny thereof having the same temperature-tolerant properties of the parent, wherein said progeny comprises said recombinant vector.

8. A plant cell, plant cell line derived therefrom, or plant portion obtained from the temperature-tolerant plant of claim 7, wherein said plant cell, plant cell line, and plant portion comprise said recombinant vector and have the same temperature-tolerant properties as said plant.

9. A temperature-tolerant higher plant that has been transformed with a gene encoding choline oxidase having an amino acid sequence of SEQ ID NO:2 or a progeny thereof having the same temperature-tolerant properties of the parent, wherein said progeny comprises said gene, and
    wherein temperature-tolerant is defined as the ability to grow at higher or lower temperatures than the temperatures which normally allow non-transformed plants of the same species to grow.

* * * * *

SEQUENCE LISTING

<160> NUMBER OF SEQ ID NOS: 8

<210> SEQ ID NO 1
<211> LENGTH: 2400
<212> TYPE: DNA
<213> ORGANISM: Arthrobacter sp.
<220> FEATURE:
<221> NAME/KEY: CDS
<222> LOCATION: (361)..(2001)

<400> SEQUENCE: 1

| | |
|---|---|
| gggaatatcc gtcgtcgtag acgagcccett cggcccgtgt aaaggtggag accttccaca | 60 |
| ccgaggacga ggccgtcgcg accgccaacg acaccaacta cgggctgtcc ggcgcggtcc | 120 |
| tggacccagg acgccggcaa gacgcagcgc gtggccggcc ggctgcgaca cggcaccgtc | 180 |
| tggatcaacg acttccaccc ctacctccca cagaccgagt ggggcggctt cggccagtcc | 240 |
| ggcgtcggcc gcgaactcgg cccgaccggc ctggccgagt accaggaggc caagcacatc | 300 |
| taccagaaca ccagcccgca ggtcaccggc tggttcgctg accacggcaa ggagaactag | 360 |

| atg cac atc gac aac atc gag aac ctg agc gac agg gag ttc gac tac | 408 |
|---|---|
| Met His Ile Asp Asn Ile Glu Asn Leu Ser Asp Arg Glu Phe Asp Tyr | |
| 1               5                   10                  15 | |

| atc gtc gtc ggc ggc ggg tcc gcc ggg gcc gcc gtc gcc gcc cgg ctg | 456 |
|---|---|
| Ile Val Val Gly Gly Gly Ser Ala Gly Ala Ala Val Ala Ala Arg Leu | |
|                 20                  25                  30 | |

| agc gag gat ccc gca gtg agc gtg gcg ctg gtg gag gcc ggc ccg gat | 504 |
|---|---|
| Ser Glu Asp Pro Ala Val Ser Val Ala Leu Val Glu Ala Gly Pro Asp | |
|         35                  40                  45 | |

| gac cgc ggc gtg ccc gag gtg ctg cag ctg gac cgc tgg atg gag ctg | 552 |
|---|---|
| Asp Arg Gly Val Pro Glu Val Leu Gln Leu Asp Arg Trp Met Glu Leu | |
| 50                  55                  60 | |

| ctg gaa tcg ggc tac gac tgg gac tac ccg atc gag ccg cag gag aac | 600 |
|---|---|
| Leu Glu Ser Gly Tyr Asp Trp Asp Tyr Pro Ile Glu Pro Gln Glu Asn | |
| 65                  70                  75                  80 | |

| ggc aac tcc ttc atg cgc cat gcc cgt gcc aag gtc atg ggc ggc tgc | 648 |
|---|---|
| Gly Asn Ser Phe Met Arg His Ala Arg Ala Lys Val Met Gly Gly Cys | |
|             85                  90                  95 | |

| tcc agc cac aac tcc tgc atc gcc ttc tgg gcc ccg cgc gag gac ctg | 696 |
|---|---|
| Ser Ser His Asn Ser Cys Ile Ala Phe Trp Ala Pro Arg Glu Asp Leu | |
|             100                 105                 110 | |

| gac gag tgg gag gcc aag tac ggc gcc acc ggc tgg aac gcc gag gcg | 744 |
|---|---|
| Asp Glu Trp Glu Ala Lys Tyr Gly Ala Thr Gly Trp Asn Ala Glu Ala | |
|         115                 120                 125 | |

| gcc tgg ccg ctg tac aag cgg ctg gaa acc aac gag gac gcg ggc ccg | 792 |
|---|---|
| Ala Trp Pro Leu Tyr Lys Arg Leu Glu Thr Asn Glu Asp Ala Gly Pro | |
| 130                 135                 140 | |

| gac gcc ccg cac cac ggg gac tcc ggc ccc gtg cac ctg atg aac gtg | 840 |
|---|---|
| Asp Ala Pro His His Gly Asp Ser Gly Pro Val His Leu Met Asn Val | |
| 145                 150                 155                 160 | |

| ccc ccg aag gac ccg acc ggc gtc gcg ctc ctg gac gcc tgc gag cag | 888 |
|---|---|
| Pro Pro Lys Asp Pro Thr Gly Val Ala Leu Leu Asp Ala Cys Glu Gln | |
|             165                 170                 175 | |

| gcc ggc atc ccg cgc gcg aag ttc aac acc ggc acc acc gtg gtc aac | 936 |
|---|---|
| Ala Gly Ile Pro Arg Ala Lys Phe Asn Thr Gly Thr Thr Val Val Asn | |
|             180                 185                 190 | |

| ggc gcc aac ttc ttc cag atc aac cgg gcg gcg gac ggc acc cgc tcc | 984 |
|---|---|
| Gly Ala Asn Phe Phe Gln Ile Asn Arg Ala Ala Asp Gly Thr Arg Ser | |
|         195                 200                 205 | |

```
tcc agc tcg gtc tcc tac atc cac ccg atc gtc gag cag gag aac ttc    1032
Ser Ser Ser Val Ser Tyr Ile His Pro Ile Val Glu Gln Glu Asn Phe
    210             215             220 acc ctg cta acc ggc ctg cgc gcc cgc cag ctg gtg ttc gac gcg gac    1080
Thr Leu Leu Thr Gly Leu Arg Ala Arg Gln Leu Val Phe Asp Ala Asp
225             230             235             240 agg cgc tgc acc ggc gtc gac atc gtg gac tcc gcc ttc ggc cgc acc    1128
Arg Arg Cys Thr Gly Val Asp Ile Val Asp Ser Ala Phe Gly Arg Thr
            245             250             255 cat cgg ctg acg gcg cgc aat gaa gtc gtg ctc tcc acc ggc gcg atc    1176
His Arg Leu Thr Ala Arg Asn Glu Val Val Leu Ser Thr Gly Ala Ile
        260             265             270 gat acg ccg aag ctg ttg atg ctc tcc gga atc ggc ccc gcc gcc cac    1224
Asp Thr Pro Lys Leu Leu Met Leu Ser Gly Ile Gly Pro Ala Ala His
    275             280             285 ctc gcc gag cac ggc atc gag gtc ctt ggt gga ctc ccc cgg cgt ggg    1272
Leu Ala Glu His Gly Ile Glu Val Leu Gly Gly Leu Pro Arg Arg Gly
290             295             300 cga gca cct gca gga cca ccc gga agg cgt ggt gca gtt cga ggc caa    1320
Arg Ala Pro Ala Gly Pro Pro Gly Arg Arg Gly Ala Val Arg Gly Gln
305             310             315             320 gca gcc cat ggt cgc cga gtc cac gca gtg gtg gga gat cgg cat ctt    1368
Ala Ala His Gly Arg Arg Val His Ala Val Val Gly Asp Arg His Leu
            325             330             335 cac ccc cac cga gga cgg cct gga ccg ccc cga cct gat gat gca cta    1416
His Pro His Arg Gly Arg Pro Gly Pro Pro Arg Pro Asp Asp Ala Leu
        340             345             350 cgg ctc cgt gcc gtt cga cat gaa cac cct gcg gca cgg cta ccc cac    1464
Arg Leu Arg Ala Val Arg His Glu His Pro Ala Ala Arg Leu Pro His
    355             360             365 cac gga gaa cgg gct tca gcc tca ccc cga acg tca cgc acg ccc gct    1512
His Gly Glu Arg Ala Ser Ala Ser Pro Arg Thr Ser Arg Thr Pro Ala
370             375             380 ccc gcg gca ctg tcc ggc tgc gca gcc gcg act tcc gcg ata agc cca    1560
Pro Ala Ala Leu Ser Gly Cys Ala Ala Ala Thr Ser Ala Ile Ser Pro
385             390             395             400 tgg tcg acc cgc gct act tca ccg acc cag aag ggc cat gac atg cgc    1608
Trp Ser Thr Arg Ala Thr Ser Pro Thr Gln Lys Gly His Asp Met Arg
            405             410             415 gtc atg gtc gcc ggc atc cgc aag gcc cgc gaa atc gcc gcc cag ccc    1656
Val Met Val Ala Gly Ile Arg Lys Ala Arg Glu Ile Ala Ala Gln Pro
        420             425             430 gcc atg gcg gaa tgg acc ggc cgc gag ctc tcc ccc ggc gtc gag gcg    1704
Ala Met Ala Glu Trp Thr Gly Arg Glu Leu Ser Pro Gly Val Glu Ala
    435             440             445 cag acc gac gag gag ctg cag gac tac atc cgc aag acg cac aac acc    1752
Gln Thr Asp Glu Glu Leu Gln Asp Tyr Ile Arg Lys Thr His Asn Thr
450             455             460 gtc tac cac ccc gtg ggc acc gtg cgc atg ggc gcg gtc gag gac gag    1800
Val Tyr His Pro Val Gly Thr Val Arg Met Gly Ala Val Glu Asp Glu
465             470             475             480 atg tcc ccg ctc gac ccc gag ctg cgg gtc aag ggc gtc acc ggt ctg    1848
Met Ser Pro Leu Asp Pro Glu Leu Arg Val Lys Gly Val Thr Gly Leu
            485             490             495 cgc gtc ggc gac gcc tcg gtc atg ccc gag cac gtg acc gtc aac ccc    1896
Arg Val Gly Asp Ala Ser Val Met Pro Glu His Val Thr Val Asn Pro
        500             505             510 aac atc acc gtc atg atg atc ggc gag cgc tgc gcg gac ctt atc cgc    1944
Asn Ile Thr Val Met Met Ile Gly Glu Arg Cys Ala Asp Leu Ile Arg
    515             520             525
```

```
tcc gcc cgc gcc ggt gaa aca acg acg gcg gac gcc gag ctg agc gcg    1992
Ser Ala Arg Ala Gly Glu Thr Thr Thr Ala Asp Ala Glu Leu Ser Ala
    530                 535                 540 gcc ctc gcc taagcgggag cggccagccg cggggcctgt ccggaaccac             2041
Ala Leu Ala
545 ctggcgggcc ccgcatgggg ccggacacaa tgccggtaac taagggtgcg gaagcagtcc   2101 tgcttccaca cccgcgtttt gcacgcccgg gccggcaact ggcccggccg gctaagccga   2161 aggtcttccg ggggcgggcc ggatcgctgc gggcagtccg tcggccagcc gctgcagcgt   2221 gccggcggta atggcggtgt aggcagggat cgcgtcgggg tagatgtact cgttgcgggc   2281 gtgcgcgccg tcgcccaccg cgcccaggcc gcacaggacc gggatgccga gggcggagac   2341 gaagttggcg tcgctgcccc cgcccaccga ggcggtttcc agctcccggc cctgctcca    2400
```

<210> SEQ ID NO 2
<211> LENGTH: 547
<212> TYPE: PRT
<213> ORGANISM: Arthrobacter sp.

<400> SEQUENCE: 2

```
Met His Ile Asp Asn Ile Glu Asn Leu Ser Asp Arg Glu Phe Asp Tyr
  1               5                  10                  15

Ile Val Val Gly Gly Ser Ala Gly Ala Val Ala Ala Arg Leu
                 20                  25                  30

Ser Glu Asp Pro Ala Val Ser Val Ala Leu Val Glu Ala Gly Pro Asp
             35                  40                  45

Asp Arg Gly Val Pro Glu Val Leu Gln Leu Asp Arg Trp Met Glu Leu
         50                  55                  60

Leu Glu Ser Gly Tyr Asp Trp Asp Tyr Pro Ile Glu Pro Gln Glu Asn
 65                  70                  75                  80

Gly Asn Ser Phe Met Arg His Ala Arg Ala Lys Val Met Gly Gly Cys
                 85                  90                  95

Ser Ser His Asn Ser Cys Ile Ala Phe Trp Ala Pro Arg Glu Asp Leu
            100                 105                 110

Asp Glu Trp Glu Ala Lys Tyr Gly Ala Thr Gly Trp Asn Ala Glu Ala
        115                 120                 125

Ala Trp Pro Leu Tyr Lys Arg Leu Glu Thr Asn Glu Asp Ala Gly Pro
    130                 135                 140

Asp Ala Pro His His Gly Asp Ser Gly Pro Val His Leu Met Asn Val
145                 150                 155                 160

Pro Pro Lys Asp Pro Thr Gly Val Ala Leu Leu Asp Ala Cys Glu Gln
                165                 170                 175

Ala Gly Ile Pro Arg Ala Lys Phe Asn Thr Gly Thr Thr Val Val Asn
            180                 185                 190

Gly Ala Asn Phe Phe Gln Ile Asn Arg Arg Ala Asp Gly Thr Arg Ser
        195                 200                 205

Ser Ser Ser Val Ser Tyr Ile His Pro Ile Val Glu Gln Glu Asn Phe
    210                 215                 220

Thr Leu Leu Thr Gly Leu Arg Ala Arg Gln Leu Val Phe Asp Ala Asp
225                 230                 235                 240

Arg Arg Cys Thr Gly Val Asp Ile Val Asp Ser Ala Phe Gly Arg Thr
                245                 250                 255

His Arg Leu Thr Ala Arg Asn Glu Val Val Leu Ser Thr Gly Ala Ile
            260                 265                 270
```

```
Asp Thr Pro Lys Leu Leu Met Leu Ser Gly Ile Gly Pro Ala Ala His
        275                 280                 285
Leu Ala Glu His Gly Ile Glu Val Leu Gly Gly Leu Pro Arg Arg Gly
        290                 295                 300
Arg Ala Pro Ala Gly Pro Pro Gly Arg Arg Gly Ala Val Arg Gly Gln
305                 310                 315                 320
Ala Ala His Gly Arg Arg Val His Ala Val Gly Asp Arg His Leu
                325                 330                 335
His Pro His Arg Gly Arg Pro Gly Pro Arg Pro Asp Asp Ala Leu
                340                 345                 350
Arg Leu Arg Ala Val Arg His Glu His Pro Ala Ala Arg Leu Pro His
        355                 360                 365
His Gly Glu Arg Ala Ser Ala Ser Pro Arg Thr Ser Arg Thr Pro Ala
        370                 375                 380
Pro Ala Ala Leu Ser Gly Cys Ala Ala Thr Ser Ala Ile Ser Pro
385                 390                 395                 400
Trp Ser Thr Arg Ala Thr Ser Pro Thr Gln Lys Gly His Asp Met Arg
        405                 410                 415
Val Met Val Ala Gly Ile Arg Lys Ala Arg Glu Ile Ala Ala Gln Pro
        420                 425                 430
Ala Met Ala Glu Trp Thr Gly Arg Glu Leu Ser Pro Gly Val Glu Ala
        435                 440                 445
Gln Thr Asp Glu Glu Leu Gln Asp Tyr Ile Arg Lys Thr His Asn Thr
        450                 455                 460
Val Tyr His Pro Val Gly Thr Val Arg Met Gly Ala Val Glu Asp Glu
465                 470                 475                 480
Met Ser Pro Leu Asp Pro Glu Leu Arg Val Lys Gly Val Thr Gly Leu
                485                 490                 495
Arg Val Gly Asp Ala Ser Val Met Pro Glu His Val Thr Val Asn Pro
                500                 505                 510
Asn Ile Thr Val Met Met Ile Gly Glu Arg Cys Ala Asp Leu Ile Arg
        515                 520                 525
Ser Ala Arg Ala Gly Glu Thr Thr Thr Ala Asp Ala Glu Leu Ser Ala
        530                 535                 540
Ala Leu Ala
545

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence:PRIMER

<400> SEQUENCE: 3
ctgtctagat gtaattaaca atggct                                    26

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence:PRIMER

<400> SEQUENCE: 4
ccacatatgc atgcattgca ctct                                      24
```

```
<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:PRIMER

<400> SEQUENCE: 5
aaccatatgc acatcgacaa catc                                              24

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:PRIMER

<400> SEQUENCE: 6
gctccatcca gcggtccagc                                                   20

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence:PRIMER

<400> SEQUENCE: 7
gaaacagtcc tgcttccaca c                                                 21

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence:PRIMER

<400> SEQUENCE: 8
gcgagctctg cctacaccgc cat                                               23
```